United States Patent
Kim

(10) Patent No.: US 11,602,605 B1
(45) Date of Patent: Mar. 14, 2023

(54) SYSTEM AND METHOD FOR AN ENDOTRACHEAL TUBE CUFF ASSEMBLY

(71) Applicant: Kevin Chong Kim, Holmdel, NJ (US)

(72) Inventor: Kevin Chong Kim, Holmdel, NJ (US)

( * ) Notice: Subject to any disclaimer, the term of this patent is extended or adjusted under 35 U.S.C. 154(b) by 0 days.

(21) Appl. No.: 17/848,273

(22) Filed: Jun. 23, 2022

(51) Int. Cl.
*A61M 16/04* (2006.01)
*A61M 16/00* (2006.01)

(52) U.S. Cl.
CPC ...... *A61M 16/044* (2013.01); *A61M 16/0003* (2014.02); *A61M 16/047* (2013.01); *A61M 16/0436* (2014.02); *A61M 16/0443* (2014.02); *A61M 16/0463* (2013.01); *A61M 16/0486* (2014.02); *A61M 2016/0027* (2013.01); *A61M 2205/0216* (2013.01)

(58) Field of Classification Search
CPC ............ A61M 16/044; A61M 16/0436; A61M 16/0443; A61M 16/0434; A61M 16/0454; A61M 16/0456; A61M 16/0459; A61M 16/0486; A61M 16/0463; A61M 16/0003; A61M 16/047; A61M 16/0477; A61M 16/0484; A61M 2016/0027
See application file for complete search history.

(56) References Cited

U.S. PATENT DOCUMENTS

| | | | |
|---|---|---|---|
| 9,132,212 B2 | 12/2015 | Clayton | |
| 2004/0255951 A1* | 12/2004 | Grey | A61M 16/04 128/207.14 |
| 2008/0078403 A1* | 4/2008 | Clayton | A61M 16/04 128/207.15 |
| 2010/0288289 A1* | 11/2010 | Nasir | A61M 16/0493 128/207.14 |
| 2012/0279500 A1* | 11/2012 | Singvogel | A61M 16/04 128/204.18 |
| 2015/0101598 A1* | 4/2015 | Wang | A61M 16/0459 128/202.16 |
| 2016/0228662 A1* | 8/2016 | Pendleton | A61M 16/0438 |
| 2017/0340216 A1* | 11/2017 | Morgan | A61M 16/0402 |
| 2019/0060594 A1* | 2/2019 | Qiu | A61M 16/0486 |
| 2021/0402120 A1 | 12/2021 | Tupper et al. | |
| 2022/0080141 A1 | 3/2022 | Göbel | |

FOREIGN PATENT DOCUMENTS

| | | | |
|---|---|---|---|
| DE | 202020101607 U1 * | 5/2020 | |
| EP | 2077865 B1 | 7/2009 | |
| WO | 2011127407 A1 | 10/2011 | |

OTHER PUBLICATIONS

English Machine Translation of DE202020101607U1 provided by PE2E (Year: 2020).*

* cited by examiner

*Primary Examiner* — Joseph D. Boecker
*Assistant Examiner* — Brian T Khong
(74) *Attorney, Agent, or Firm* — Loza & Loza, LLP; Jessica W. Smith

(57) ABSTRACT

A cuff assembly for an airway tube includes an outer bladder and an inner cuff. The inner cuff is positioned adjacent to the airway tube, and the outer bladder is positioned adjacent to the inner cuff. The outer bladder is made with a less elastic material and operates at a higher relative pressure. The inner cuff is made with a more elastic or hyper-elastic material and operates at a lower relative pressure. A pressure controller independently adjusts the pressure within the inner cuff and the outer bladder. A secretion collection receptacle is formed by the cuff assembly and is evacuated via a suction catheter or channel.

19 Claims, 14 Drawing Sheets

SYSTEM AND METHOD FOR AN ENDOTRACHEAL TUBE CUFF ASSEMBLY

FIELD

This application relates to system and methods for a cuff assembly implemented in a medical device and more particularly, a cuff assembly implemented within endotracheal tube, a pressure regulation system for the cuff assembly and a secretion clearance system.

BACKGROUND

Currently, there are two main types of cuffs, low volume, high pressure (LVHP) cuffs and high volume, low pressure (HVLP) cuffs. The first type, LVHP cuffs, are made from stiffer, relatively inelastic materials. Due to their inherent stiffness, a greater level of pressure (50 cm H2O to 100 cm H2O) is required to inflate LVHP cuffs. As a result, LVHP cuffs cause an excessively high pressure on the tracheal mucosa, even when inflated to a minimum pressure to create a seal with the tracheal wall. This high pressure causes an unacceptably high incidence of tracheal ischemia and necrosis, e.g., a 5%-20% incidence rate. Despite that, one crucial advantage of LVHP cuffs, when inflated, is the relative absence of folds or wrinkles, resulting in superior tracheal sealing. LVHP cuffs were first employed in the 1960's, but, today, have been widely replaced by HVLP cuffs.

HVLP cuffs are composed of more elastic, compliant materials that inflate at lower pressures. To compensate for the lower pressure characteristics and create a seal against the tracheal wall, the diameter of the HVLP cuffs are generally 1.5-2 times the diameter of the trachea when fully inflated. However, the increased volume of the HVLP cuffs requires a significant amount of cuff material that adds bulkiness to the HVLP cuff making it more difficult to intubate. Moreover, the excess material has a tendency to form wrinkles or folds due to "incomplete inflation." These wrinkles or folds often create paths for orogastric secretions to pass beyond the HVLP cuff, ultimately leading to microaspiration and infection of the lungs.

In examining the effect of cuff pressure on the trachea, it is important to keep in mind that the tracheal wall mucosa capillary perfusion pressure in humans ranges from 22 to 32 mmHg, and tracheal mucosal blood flow may be compromised at applied pressures above 30 cm H2O (22 mmHg), with total occlusion of flow to certain parts at 50 cm H2O (37 mmHg). It is apparent, then, that there is only a small overlap between the safety pressure range and that of complication. The window of efficacy and safety, indeed, is very narrow, if nonexistent.

The required pressure for typical HVLP cuffs to achieve a reasonable inflation with an acceptable number of folds or wrinkles is about 32 cm H2O. The guidelines established by various medical societies and organizations recommend maintaining the HVLP cuff pressure within a range of 20 cm H2O to 30 cm H2O to avoid occlusion of tracheal mucosal blood flow. Nevertheless, even with a strict adherence to the recommendations, many patients are still placed in harms' way. In fact, a study has shown that about 10% of patients on mechanical ventilation develop ventilator-associated pneumonia (VAP), and the mortality rate in VAP is estimated at 13%. In addition, patients with VAP face a longer hospital course and incur higher healthcare costs than similarly ill patients without VAP. Given that in the U.S., there are approximately 750,000 patients annually that require ventilation, the human and financial tolls of VAP is enormous.

Unfortunately, studies have shown that even at pressures up to 60 cm H2O, microaspiration still occurs with HVLP cuffs, suggesting the continued presence of cuff wrinkles, allowing the passage of secretions, even at higher pressures. So, even though HVLP cuffs appear superior because they are capable of producing a seal at a lower pressure level and avoiding necrosis of the tracheal wall, they are still far from being ideal.

While the principal goals of the tracheal cuff, to provide a maximum airway seal and cause minimal damage to the airway, is simple and straightforward, successfully achieving these goals has been elusive. This failure continues despite the diverse modifications and advances that have been made vis-a-vis materials, shape, and volumetric structure. Thus, there is a need for an improved cuff system that helps to reduce microaspiration and infection of the lungs by maintaining a good seal with the tracheal wall but without unduly harming the tracheal wall.

SUMMARY

In one aspect, a medical device includes an endotracheal tube configured to fit within a trachea and a cuff assembly implemented at an inferior end of the endotracheal tube. The cuff assembly includes an inflatable inner cuff with an inner surface and an outer surface, wherein the inner surface is positioned adjacent to the endotracheal tube and wherein the inner cuff has a first elasticity and an inflatable outer bladder positioned adjacent to the outer surface of the inner cuff, wherein the outer bladder has a second elasticity that is less than the first elasticity of the inner cuff.

In another aspect, a cuff assembly includes an inflatable inner cuff with an inner surface and an outer surface, wherein the inner surface is positioned adjacent to an endotracheal tube and wherein the inner cuff has a first elasticity. The cuff assembly further includes an inflatable outer bladder positioned adjacent to the outer surface of the inner cuff, wherein the outer bladder has a second elasticity that is less than the first elasticity of the inner cuff.

In another aspect, a secretion clearance system for an endotracheal tube, comprising a secretion collection receptacle positioned at a proximal end of a cuff assembly, wherein the cuff assembly is disposed around a circumference of the endotracheal tube. The system further includes a suction channel including a distal end in proximity to the secretion collection receptacle and a proximal end of the suction channel at a proximal end of the endotracheal tube, wherein the proximal end of the suction channel is in fluid communication with a vacuum.

In one or more of the above aspects, the inner cuff is configured to be inflated within a first pressure range and the outer bladder is configured to be inflated within a second pressure range, wherein the first pressure range is less than the second pressure range. For example, the inner cuff is configured to be inflated to a pressure within a range of 10 cm H2O to 20 cm H2O and the outer bladder is configured to be inflated to a pressure within a range of 50 cm H2O to 150 cm H2O.

In one or more of the above aspects, an outer surface of the outer bladder is configured to have a relatively smooth surface during inflation.

In one or more of the above aspects, a first inflation lumen is coupled to an interior of the inner cuff and a second inflation lumen is coupled to an interior of the outer bladder.

In one or more of the above aspects, the inner cuff comprises a relatively elastic material, wherein the relatively elastic material includes one or more of: silicone, latex, polyvinyl chloride (PVC), silicone, neoprene, polyisoprene, or polyurethane (PU).

In one or more of the above aspects, the outer bladder comprises a relatively inelastic material, wherein the relatively inelastic material includes one or more of: polyethylene teraphthalate (PETP), low-density polyethylene (LDPE), polyvinyl chloride (PVC), silicone, neoprene, polyisoprene, or polyurethane (PU).

In one or more of the above aspects, a pressure regulator is configured to adjust a first pressure in the inner cuff using a first pneumatic pathway and adjust a second pressure in the outer bladder using a different, second pneumatic pathway, wherein the first pressure in the inner cuff is less than the second pressure in the outer bladder.

In one or more of the above aspects, a pressure sensor device is positioned between the inner cuff and the outer bladder, wherein the pressure sensor device measures an intercuff pressure.

In one or more of the above aspects, the pressure regulator is configured to at least adjust the first pressure in the inner cuff and the second pressure in the outer bladder in response to the intercuff pressure.

In one or more of the above aspects, a first lumen extends from the endotracheal tube to the inner cuff, wherein the first lumen is fluidly coupled to the inner cuff and, a second lumen extends from the endotracheal tube to the outer bladder, wherein the second lumen is fluidly coupled to the outer bladder.

In one or more of the above aspects, a pressure regulator system is configured to maintain a first pressure within the inner cuff using the first lumen to add or remove air from the inner cuff and to maintain a second pressure within the outer bladder using the second lumen to add or remove air from the outer bladder, wherein the first pressure is less than the second pressure.

In one or more of the above aspects, a first air pump and a first release valve fluidly coupled to the first lumen and configured to add or remove air from the inner cuff, and a second air pump and a second release valve fluidly coupled to the second lumen and configured to add or remove air from the outer bladder.

In one or more of the above aspects, a pressure sensor device is positioned between the inner cuff and the outer bladder, wherein the pressure sensor device measures an intercuff pressure and wherein the pressure regulator system is configured to adjust the first pressure in the inner cuff and the second pressure in the outer bladder in response to the intercuff pressure.

In one or more of the above aspects, the secretion clearance receptacle includes an outer wall of the cuff assembly that extends proximally from a proximal surface of the cuff assembly forming a trough for collection of secretions, wherein the trough is positioned at least on a posterior side of the endotracheal tube and a proximal slanted surface that slants inwardly from the outer wall towards the top surface of the cuff assembly forming a trough for collection of secretions.

In one or more of the above aspects, the secretion collection receptacle includes an outer wall extending from a proximal end of the outer bladder to form a trough with a proximal surface of the inner cuff and/or a proximal surface of the outer bladder.

In one or more of the above aspects, the suction channel includes a catheter. A catheter guide is configured for holding the catheter, wherein the catheter guide is positioned on an anterior side of an outer surface at a proximal end of the endotracheal tube. The catheter guide rotates circumferentially to a position on a posterior side of the outer surface at a distal end of the endotracheal tube.

In one or more of the above aspects, the suction channel is positioned internally to the endotracheal tube and extends on a posterior portion of an interior wall of the endotracheal tube. The endotracheal tube forms an opening in proximity to the secretion collection receptacle, wherein the hollow channel is in fluid communication with the secretion collection receptacle through the opening for evacuation of secretions.

DETAILED DESCRIPTION

Figure 1:
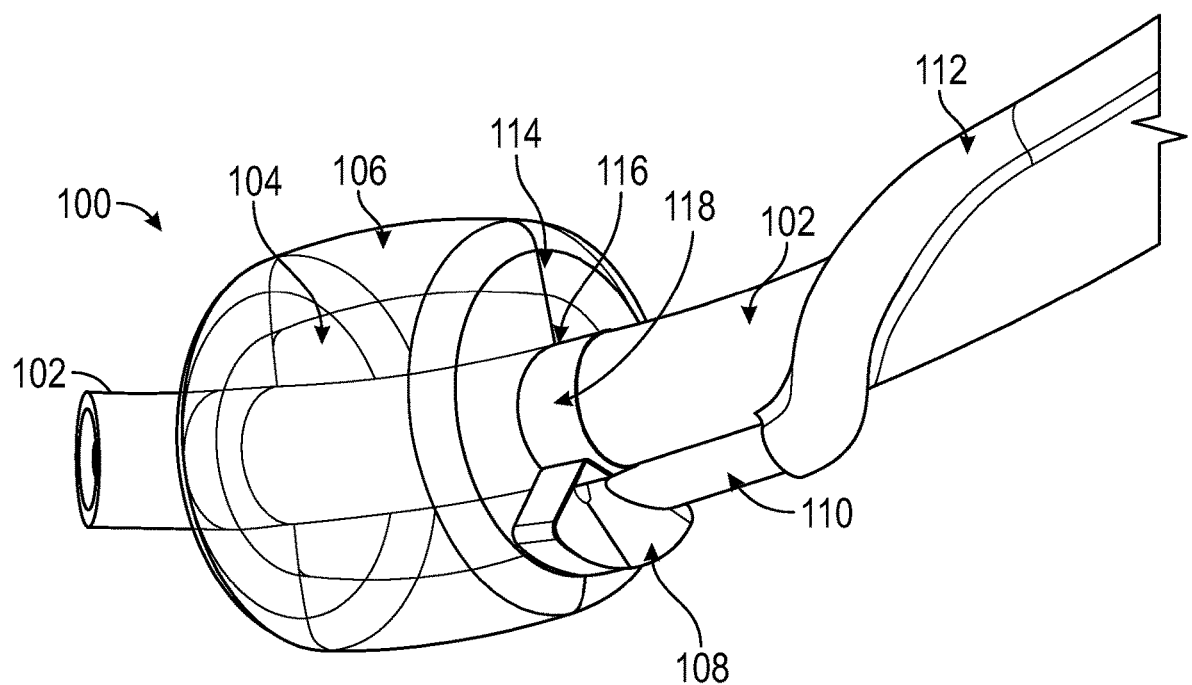
FIG. 1 illustrates an exemplary embodiment of a cuff system implemented with an endotracheal tube.

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Overview

A cuff assembly, a pressure regulation system, and a subglottic secretion clearance system are described herein that effectuate ventilation and protection of intubated patients. The cuff assembly comprises a torus-shaped outer bladder and an inner cuff. The inner cuff is positioned adjacent to an outer surface of an airway tube, and the outer bladder is positioned adjacent to an outer surface of the inner cuff. The outer bladder comprises a less elastic material and behaves as a low volume, high-pressure (LVHP) structure such that when inflated, it exhibits less folds for a more optimal tracheal seal. The inner cuff comprises a more elastic or hyper-elastic material such that it behaves as a high-volume, low-pressure (HVLP) structure.

The inner cuff and the outer bladder are each connected to a different one of two separate inflating tubes, such that the pressure of each compartment is controlled separately. Disposed between the inner cuff and the outer bladder is an intercuff pressure sensor that effectively measures the tracheal wall pressure. The pressure regulation system receives input from the intercuff pressure sensor and/or other pressure sensors. The pressure regulation system automatically monitors and adjusts the air pressure of the inner cuff and the outer bladder at preset intervals in response to the input from the pressure sensors.

The secretion clearance system includes a secretion receptacle and suction catheter. In an embodiment, the secretion receptacle is formed by a proximal portion of the cuff assembly. For example, the outer bladder extends proximally further than the proximal end of the inner cuff (the outer bladder extension). The outer bladder extension is configured such that its peripheral wall extends further or has a greater length than its inner wall. In this manner, the proximal surface of the outer bladder extension slopes distally from the peripheral surface of the outer wall to a junction between the inner cuff and the outer bladder. The suction catheter evacuates secretions accumulated in the receptacle. A guide or conduit for the suction catheter extends from the secretion collection receptacle to a proximal end of the airway tube. At a proximal end of the airway tube, the catheter guide is positioned on an anterior side of the airway tube such that it fits between the vocal cords of an intubated patient. The catheter guide extends circumferentially to lay on a posterior side of the airway tube at an distal end of the airway tube to position the catheter in proximity to the secretion receptacle.

Alternatively, the suction catheter and suction catheter guide are replaced with a channel provided in the posterior wall of the endotracheal tube. The suction channel may be circular or elliptical and has the cross-sectional area between 10 to 20 square mm. The proximal channel opening, located by the proximal end of an endotracheal tube, makes a fluid communication with a suction catheter that may then connect to vacuum. The distal opening of the suction channel fluidly communicates with the secretion collection cavity.

Embodiments of the Cuff Assembly

The cuff assembly is now described in more detail. Unlike previously known endotracheal tube cuffs, the present embodiments described herein introduce a novel cuff system that comprises at least two separately-controlled inflating bladders.

A high-pressure outer bladder is attached to the outer surface of an airway endotracheal tube by means of an inner cuff. The inner cuff couples to a distal end of the endotracheal tube. The second, outer bladder couples to an outer surface of the inner cuff. The inner cuff is a low-pressure inflatable cuff and is configured to function at a low pressure range of 10 cm H2O to 20 cm H2O. In contrast, the outer inflating bladder is configured to inflate to a high pressure range of 50 cm H2O to 150 cm H2O. The inner cuff thus operates in a pressure range that is less than the pressure range of the outer bladder.

FIG. 1 illustrates an embodiment of the cuff assembly 100 implemented with an endotracheal tube 102. The endotracheal tube 102 is a conduit configured for placement intraorally into the trachea to provide oxygenated air and/or other gases and medication to the lungs of a patient. The endotracheal tube 102 may comprise a soft polyvinyl chloride (PVC) material. Though an endotracheal tube 102 is described herein, the cuff assembly 100 may be implemented in conjunction with any suitable medical device, including, but not limited to, a tracheostomy tube or other airway tube, a catheter, a stent, and/or a feeding tube.

Typically, the cuff assembly 100 is disposed, adhesively or otherwise, towards a distal end of the endotracheal tube 102. The cuff assembly 100 includes a first donut- or torus-shaped inner cuff 104 positioned around and adjacent to the endotracheal tube 102. The inner cuff 104 is inflatable and configured to inflate radially from the endotracheal tube 102. A second, torus-shaped outer bladder 106 is positioned around and adjacent to the inner cuff 104 wherein at least a portion of the inner cuff 104 lays between the outer bladder 106 and the endotracheal tube 102. The outer bladder 106 is configured to inflate radially from the inner cuff 104 such that an outer surface of the outer bladder 106 contacts the trachea wall. In an embodiment, as seen in FIG. 1, the top surface 114 of the outer bladder 106 may extend over a top surface of the inner cuff 104 and be sealed at a junction 116 with the inner cuff 104 and/or with the endotracheal tube 102. A band 118 may secure and/or attach the cuff assembly 100 to the endotracheal tube 102.

The inner cuff 104 comprises a relatively elastic material while the outer bladder 106 comprises a relatively inelastic material, e.g., the material of the outer bladder is less elastic than the material of the inner cuff 104. For example, the relatively elastic material of the inner cuff may include one or more of: silicone, latex, polyvinyl chloride (PVC), silicone, neoprene, polyisoprene, or polyurethane (PU). The relatively inelastic material of the outer bladder 106 may include one or more of: polyethylene teraphthalate (PETP), low-density polyethylene (LDPE), polyvinyl chloride (PVC), silicone, neoprene, polyisoprene, or polyurethane (PU).

The outer bladder 106 and inner cuff 104 are configured to inflate to and maintain different pressures. The relatively elastic inner cuff is configured to operate in an inflated state at a lower pressure, e.g. in a pressure range of 10 cm H2O to 20 cm H2O. In contrast, the less elastic or relatively inelastic outer bladder is configured to operate in an inflated state at a higher pressure range of 50 cm H2O to 150 cm H2O.

In use, e.g., when inserted into a trachea and then pressurized to an inflated state, the first, inner cuff 104 behaves as a HVLP type cuff while the second, outer bladder 106 behaves as a LVHP type cuff. The more compliant inner cuff 104 is able to temper the pressure applied on the tracheal wall (the "tracheal pressure") by the higher pressurized outer bladder 106. In other words, the lower pressure, more elastic inner cuff 104 is configured to absorb excessive pressure that may otherwise be exerted on the tracheal wall by the outer bladder 106. For example, since the inner cuff 104 is more compliant and elastic, the cuff assembly 100 applies a lower total pressure/force against the tracheal wall, e.g., lower than the outer bladder pressure. The force of the inner cuff 104 acts radially on the outer bladder 106 and is thus the force ultimately exerted on the trachea as the tracheal pressure. So, the radial force produced by the inner cuff 104 and acted upon the outer bladder 106, then, is the tracheal pressure. For example, when the outer bladder intracuff pressure is greater than that of the inner cuff, and the outer bladder is inflated so that the outer surface touches the trachea, the intracuff pressure of the inner cuff is the same as the tracheal pressure.

In addition, the outer bladder 106 in an inflated state forms a relatively smooth surface with fewer folds or wrinkles, e.g. than a LVHP cuff. This reduction in wrinkles reduces the risk for leakage and creates a more uniform tracheal seal.

In this way, the cuff assembly 100 utilizes an innovative system to titrate the tracheal pressure thereby reducing tracheal complications. By incorporating the characteristics of HVLP and LVHP cuffs into one system, the cuff system 100 exploits the advantages found in both types of cuffs: superior tracheal seal and greater safety to the trachea. The cuff system 100 features the advantages of superior seal against the tracheal wall with reduced tracheal damage. The cuff assembly 100 thus helps protect the lungs from being contaminated with orogastric contents or blood without undue harm to the tracheal wall.

In an embodiment, the cuff assembly 100 may also include a secretion collection system implemented to collect and remove aspirations or other fluids that may accumulate around a proximal end of the cuff assembly 100. The secretion collection system includes a secretion collection receptacle 108 positioned on a proximal end of the cuff system 100. A suction catheter 110 is configured to evacuate the receptacle 108 and is positioned in or adjacent to the receptacle 108 on a posterior side of the endotracheal tube 102. A catheter guide 112 may enclose the catheter 110 on an outer surface of the tube 102.

Figure 2:
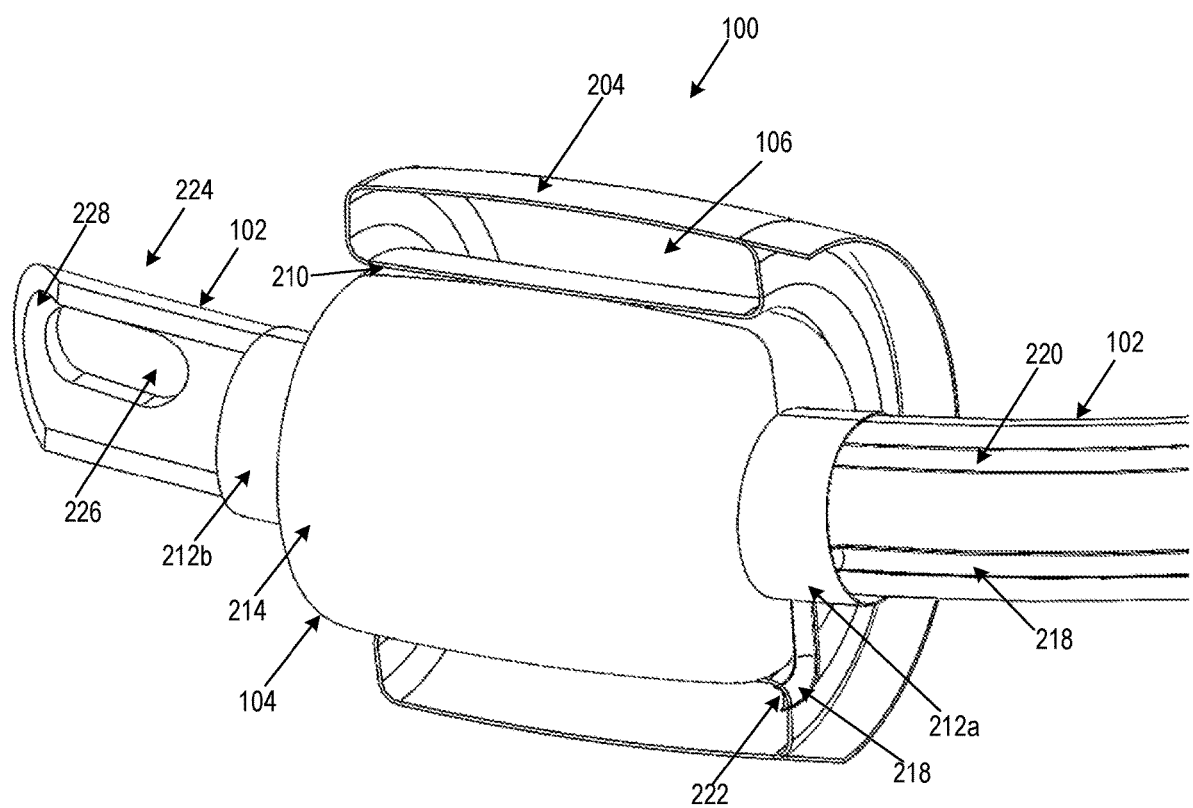
FIG. 2 illustrates an exemplary embodiment of the cuff system with a cross-section of the outer bladder.

FIG. 2 illustrates the cuff system 100 with a cross-section of the outer bladder 106. In this embodiment, the outer bladder 106 is a self-contained structure, e.g. it has separate walls from the inner cuff 104 and endotracheal tube 102. The outer bladder 106 includes an inner surface 210 and outer surface 204. The inner surface 210 of the bladder 106 is positioned adjacent to an outer surface 214 of the inner cuff 104 and may be attached to the outer surface 214 of the cuff 104 using, e.g., one or more of adhesives, heat or by other means.

The outer bladder 106 is configured for inflation and deflation via a first lumen 218 in communication with the outer bladder 106 through an opening 222 formed in the lumen 218. The lumen 218 may be positioned in or attached to an interior or an exterior of the endotracheal tube 102 and extend to a proximal end of the endotracheal tube 102.

The inner cuff 104 has a proximal band 212a and a distal band 212b extending from the outer surface 214 of the cuff walls. These bands 212a, 212b are sized to accommodate the endotracheal tube 102. The proximal band 212a is located farther away from the distal end of the endotracheal tube 102, and the distal band 212b located closer to the distal end of the endotracheal tube 102. The bands 212a, 212b assist in coupling the inner cuff 104 to the endotracheal tube 102 and may further attach to the endotracheal tube 102 using adhesives, heat or by other means.

The inner cuff 104 is configured for inflation and deflation via a second lumen 220 in communication with the inner cuff 104 through a hole (not shown), such as an opening or notch, in the lumen 220. The second lumen 220 may be positioned in or attached to an interior or an exterior of the endotracheal tube 102 and extend to a proximal end of the endotracheal tube 102.

A tip 224 of the endotracheal tube 102 forms a window 226 and/or an opening 228 for passage of oxygenated air to the trachea. Though described with an endotracheal tube 102, the cuff assembly 100 as provided herein may be used in conjunction with any suitable medical device, including, but not limited to, other types of airway tubes, catheters, stents, and/or feeding tubes.

Figure 3A:
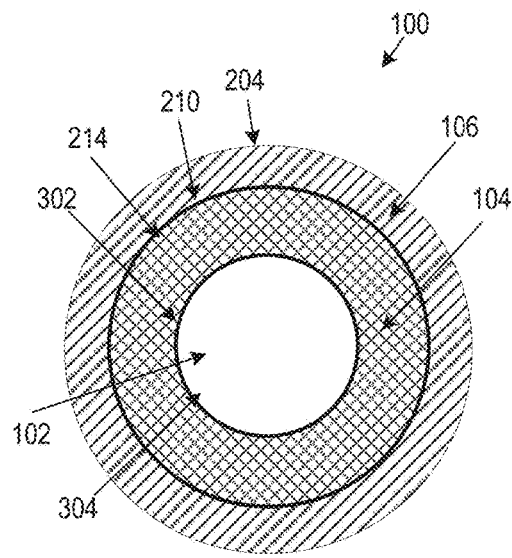
FIGS. 3A-D illustrate cross-sectional views of exemplary embodiments of the cuff system.
Figure 3B:
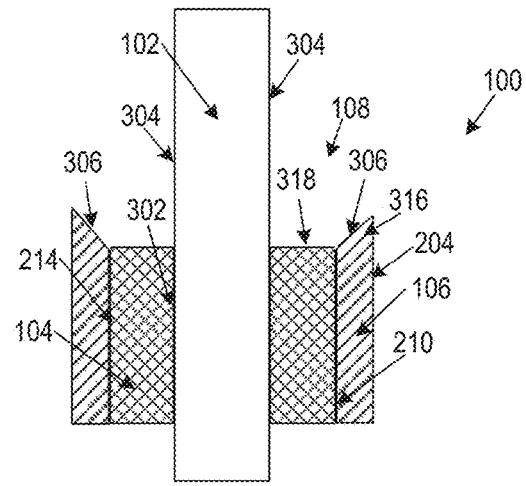

FIGS. 3A-B illustrate cross-sectional views of an embodiment of the cuff system 100. FIG. 3A illustrates a top cross-sectional view of the cuff system 100, and FIG. 3B illustrates a side cross-sectional view of the cuff system 100. As seen in FIG. 3A, the outer bladder 106 is an inflatable torus or donut-shaped, self-contained structure with an outer surface 204 and inner surface 210. Similarly, the inner cuff 104 is an inflatable torus or donut shaped, self-contained structure with an outer surface 214 and an inner surface 302.

The inner surface 210 of the outer bladder 106 is proximate to and/or attached to the outer surface 214 of the inner cuff 104. The inner surface 302 of the inner cuff 104 is proximate to and/or attached to an outer surface 304 of the endotracheal tube 102. As such, at least a portion of the inner cuff 104 is positioned between the outer bladder 106 and the endotracheal tube 102.

In an embodiment, as seen in FIG. 1, the proximal surface 306 of the outer bladder 106 extends to the inner cuff 104 and is sealed at a junction with a top surface 318 of the inner cuff 104 and/or with the endotracheal tube 102. The proximal surface 306 of the bladder 106 thus prevents leakage between the inner cuff 104 and the outer bladder 106. Alternatively or additionally, the outer surface 214 of the inner cuff 104 may be attached to form a seal against leakage or pressed against the inner surface 210 of the outer bladder 106, e.g. such that secretions or other matter may not leak through the junction. For example, the inner cuff 104 and outer bladder 106 may be adhesively attached or attached using a heating process or a combination thereof.

In addition, the inner surface 302 of the inner cuff 104 is sealed or attached to or pressed against the outer surface 304 of the endotracheal tube 102 to prevent leakage. For example, the inner cuff 104 and endotracheal tube 102 may be adhesively attached or attached using a heating process or a combination thereof. These seal or attachment prevents the leakage of secretions between the endotracheal tube 102 and the inner cuff 104.

In another embodiment shown in FIG. 2 and this FIG. 3B, a secretion collection receptacle 108 may be formed using an outer surface 204 of the outer bladder 106 to form a wall 316. For example, a portion of the outer surface 204 of the outer bladder 106, e.g. on a proximal side of the cuff assembly 100, extends upwards from a proximal surface 318 of the inner cuff 104. The proximal surface 306 of the outer bladder 106 may slant from the wall 316 inwardly towards the proximal top surface 318 of the inner cuff 104 to form a valley or trough around at least a portion of a circumference of the endotracheal tube 102, e.g. at least on a posterior side of the endotracheal tube 102. This valley or trough of the secretion collection receptacle 108 collects secretions or particulates that may be removed using suction catheter 110, as described further herein. In another embodiment shown in FIG. 2 and FIG. 11B, the wall 316 of the outer bladder 106 does not slant at an angle. The outer surface 204 of the outer bladder forms a flat or relatively flat wall 316 that extends proximately and at a relatively perpendicular angle with respect to the top surface 318 of the inner cuff 104.

Figure 3C:
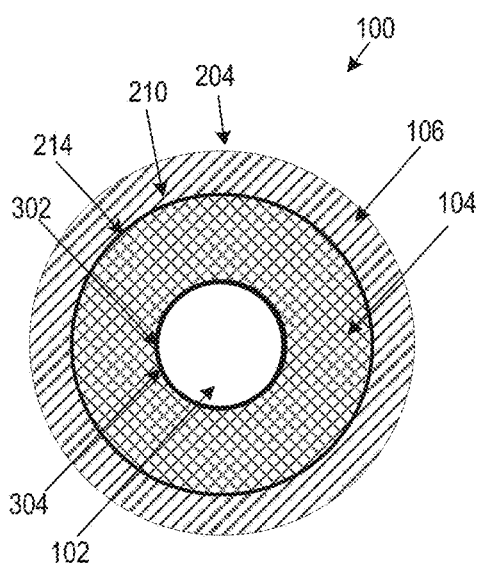
Figure 3D:
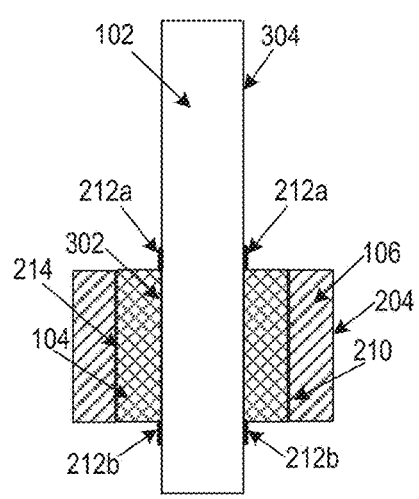

FIGS. 3C and 3D illustrate another embodiment of the cuff system 100 in which the inner cuff 104 is formed at least partially using an outer surface 304 of the endotracheal tube 102. In this example, the inner surface 302 of the inner cuff 104 is formed by the outer surface 304 of the endotracheal tube 102. The outer surface 214 of the inner cuff 104 is attached with an airtight seal to the outer surface 304 of the endotracheal tube 102. For example, the outer surface 214 of the inner cuff may form band 212a, 212b encircling the endotracheal tube 102 to form the airtight seal to the endotracheal tube 102.

One or more features of the various embodiments in FIG. 3A-D may be employed in any of the embodiments shown herein.

Figure 4:
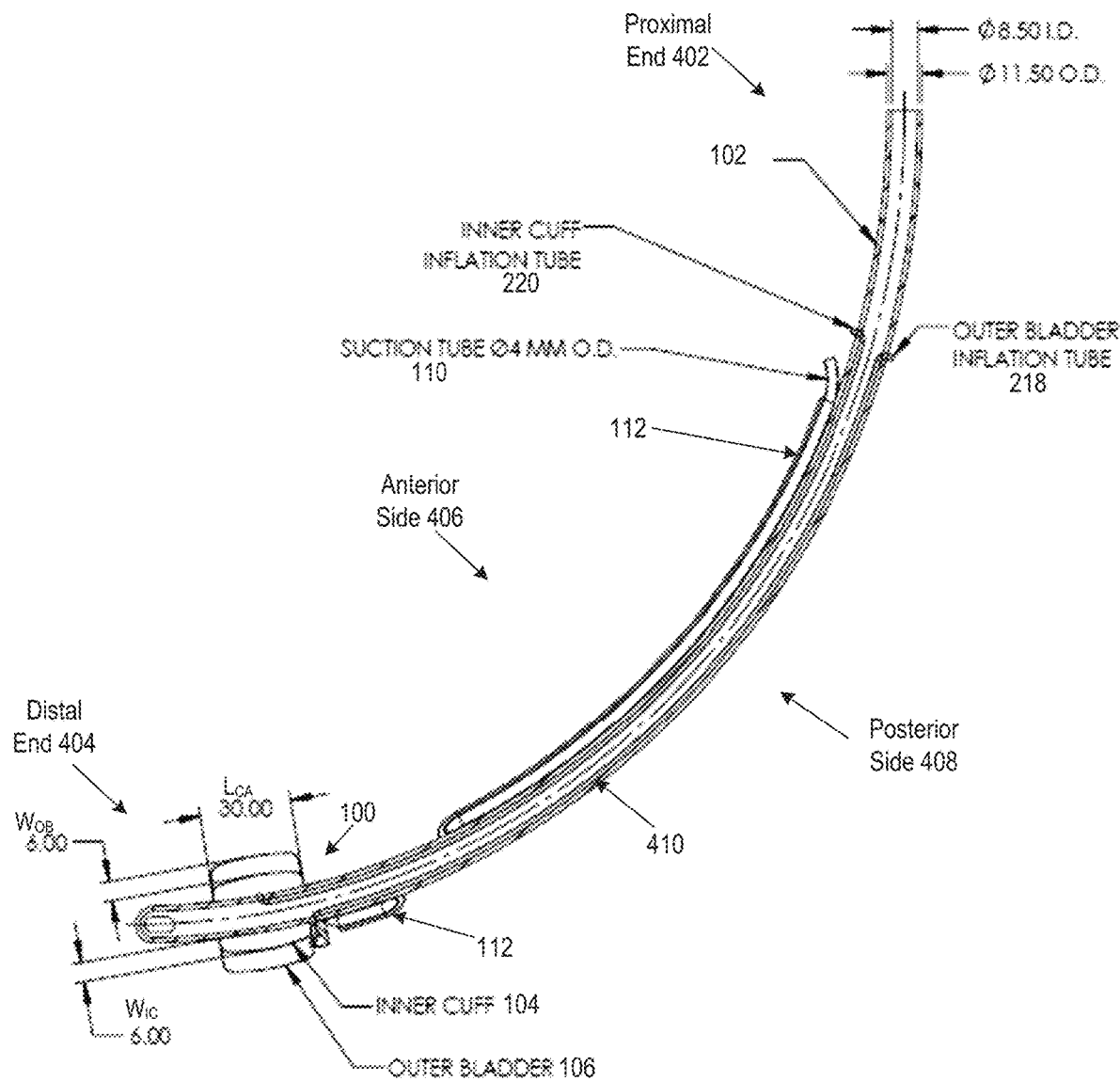
FIG. 4 illustrates a cross-sectional view of an exemplary embodiment of the cuff assembly implemented with the endotracheal tube.

FIG. 4 illustrates a cross-sectional view of the cuff assembly 100 implemented with the endotracheal tube 102. In an embodiment, the inner cuff inflation tube 220 and the outer bladder inflation tube 218 extend from the cuff assembly 100 at a distal end 404 of the endotracheal tube 102 to a proximal end 402 of the endotracheal tube 102. The inner cuff inflation tube 220 and the outer bladder inflation tube 218 are positioned in, or on an interior or an exterior of the endotracheal tube 102, e.g. attached to an interior wall 410 of the endotracheal tube 102. In another embodiment, inner cuff inflation tube 220 and the outer bladder inflation tube 218 are positioned on an exterior surface 304 of the endotracheal tube 102.

In an embodiment, the catheter guide 112 is positioned at a posterior side 408 of the endotracheal tube 102 in proximity to the secretion collection receptacle 108. The catheter guide 112 then extends circumferentially around the endotracheal tube 102 to lay on an anterior side 406 of the endotracheal tube 102 at a proximal end of the tube 102. The suction tube 110 lies within the catheter guide 112 and may be replaced in the event of a clog or other malfunction.

In an embodiment, the inner cuff 104 and the outer bladder 106 have an approximately equal length $L_{CA}$. For example, the length of the cuff assembly $L_{CA}$ is approximately 30 millimeters (mm). In other embodiments, one or more of the inner cuff 104 or the outer bladder 106 are longer or shorter than the length of the other.

In addition, in an embodiment, the width of the outer bladder $W_{OB}$ and the width of the inner cuff $W_{IC}$ are approximately equal. For example, the width of the outer bladder $W_{OB}$ and the width of the inner cuff $W_{IC}$ are approximately 6 mm. In other embodiments, the width of the outer bladder $W_{OB}$ or the width of the inner cuff $W_{IC}$ may be different, e.g. the inner cuff 104 may be wider or less wide than the outer bladder 106. The inner cuff 104 and the outer bladder 106 may have a thickness of approximately 0.00086 inches (0.022 mm) or less.

In another example, the inner diameter of the endotracheal tube 102 is approximately 8.5 mm and the outer diameter of the endotracheal tube is approximately 11.5 mm. The length of the endotracheal tube 102 is approximately 400 mm. These dimensions are exemplary, and the cuff assembly 100 may be implemented with other endotracheal tubes with alternative dimensions or with other medical devices having various sizes and dimensions. In addition, the exemplary size and dimensions of the cuff assembly 100 described herein may be modified depending on the medical device and implementation.

Figure 5A:
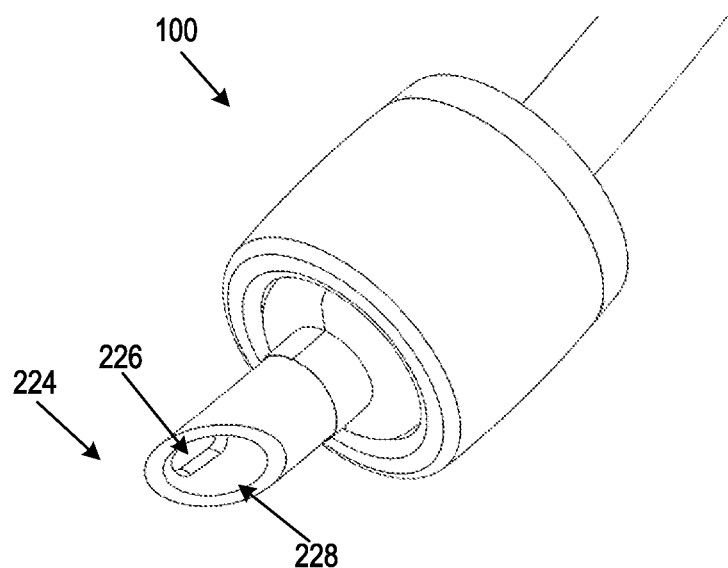
FIGS. 5A-B illustrate an exemplary embodiment of a tip of the endotracheal tube in more detail.
Figure 5B:
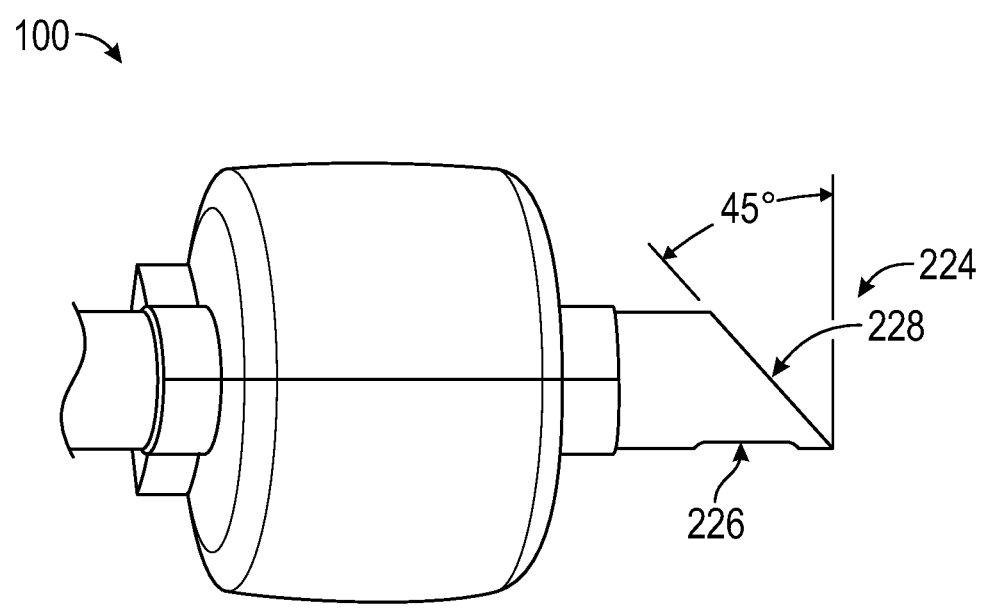

FIG. 5A and FIG. 5B illustrate an exemplary embodiment of the tip 224 of the endotracheal tube 102 in more detail. The tip 224 is positioned at the distal end 404 of the endotracheal tube 102 on the distal end of the cuff assembly 100. The tip 224 may form an opening 228 with slanted walls, e.g. the walls may form an approximate 45 degree angle. Additionally or alternatively, a window 226 is formed on a side of the tip 224. The tip 224 may thus include two openings 226, 228 for passage of oxygenated air to the trachea.

The cuff assembly 100 provides for an improved seal against the tracheal wall because the higher pressure, outer bladder 106 forms a relatively smooth surface with fewer folds or wrinkles, e.g. than a HVLP cuff. In addition, the lower pressure, inner cuff 104 creates a low total pressure against the tracheal wall by the cuff assembly 100, e.g. similar to or less than the pressure of typical HVLP cuffs, but with an improved seal against the tracheal wall. The tracheal mucosa is thus subjected to a low total pressure, and a lower risk for an ischemic injury. The cuff assembly 100 also has less bulkiness than a HVLP cuff, making it easier to intubate a patient.

Embodiments of the Pressure Regulation System

The benefit and risks of the endotracheal tube, more than the tube itself, depends on maintaining a predetermined pressure range in the cuff assembly. For example, overinflation of the cuff assembly may result in tracheal mucosal injury by causing ischemic damage and vocal cord nerve injury. The damage is due to the constant pressure exerted by the cuff that prevents blood flow to the mucosa of the trachea. This loss of blood may lead tissue necrosis. In addition, damage may also arise due to the repeated abrasion from the cuff moving against the tracheal wall. When the cuff is underinflated and the tracheal seal is inadequate, the patient may not receive sufficient oxygen. Further, the patient is subjected to increased possibility of pneumonia from the aspiration of orogastric content. Thus, maintenance of the pressure of the cuff assembly 100 for an endotracheal tube 102 is a critical component of patient care, vis-a-vis reduction of tracheal injury and prevention of ventilator-associated pneumonia (VAP).

Currently, several types of automated cuff pressure regulators are available. These current devices monitor an intracuff pressure within a single cuff. However, a close examination reveals a major flaw in this approach. The intracuff pressure does not reflect the precise pressure applied to the tracheal wall. Ultimately, it is the tracheal wall pressure that determines both the risks and benefits of the cuff. Thus, there is a need for an improved system and method to monitor and regulate the cuff pressure.

Figure 6:
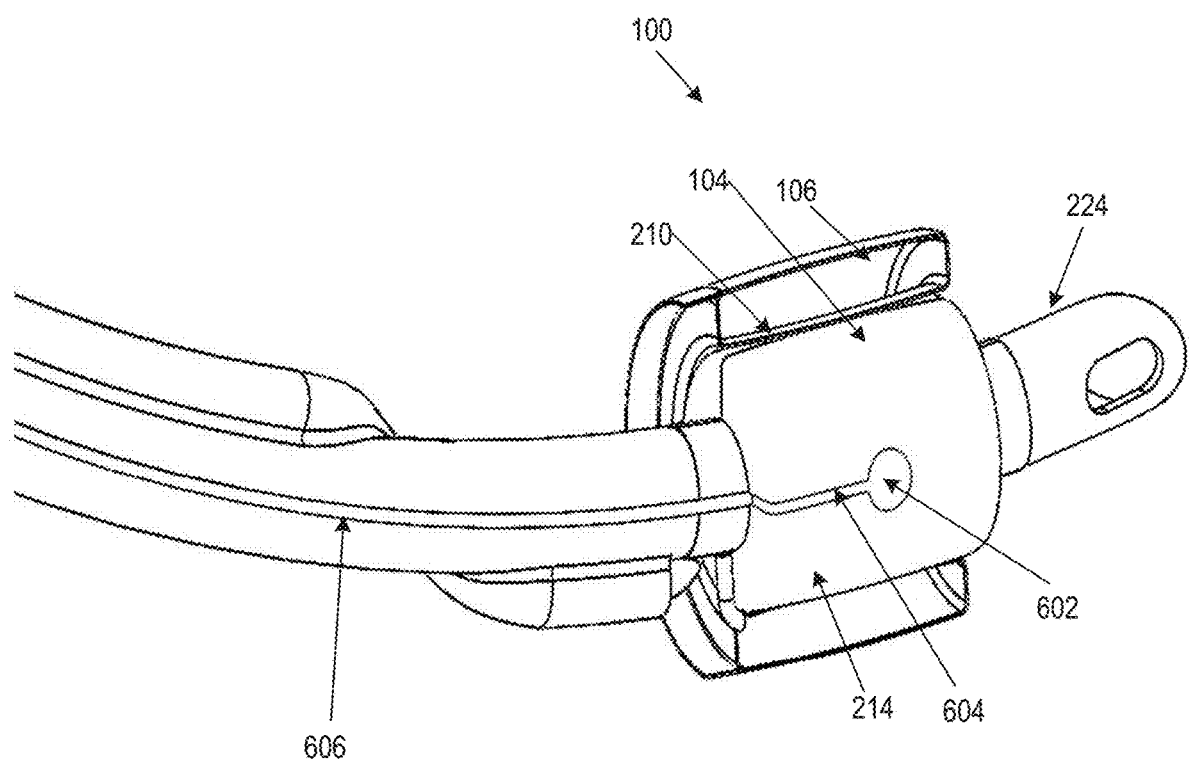
FIG. 6 illustrates an exemplary embodiment of an intercuff pressure sensor device in the cuff assembly.

FIG. 6 illustrates an embodiment of an intercuff pressure sensor device 602 in the cuff assembly 100. In this embodiment, a pressure regulation system monitors the tracheal pressure by utilizing at least the intercuff pressure sensor device 602 positioned between the inner cuff 104 and the outer bladder 106. The pressure sensor device 602 may be fixedly attached to the outer surface 214 of the inner cuff 104 or may be fixedly attached to the inner surface 210 of the outer bladder 106.

The force of the inner cuff 104 acts radially on the outer bladder 106 and is thus the force ultimately exerted on the trachea wall as the tracheal pressure. So, the radial force produced by the inner cuff 104 and acted upon the outer bladder 106, then, is the resulting tracheal pressure. For example, when the outer bladder intracuff pressure is greater than that of the inner cuff 104, and the outer bladder 106 is inflated so that the outer surface 204 touches the tracheal wall, the radial force of the inner cuff 104 against the outer bladder 106 is the resulting pressure against the tracheal wall. Since the intercuff pressure sensor device 602 is positioned between the inner cuff 104 and the outer bladder 106, it measures the radial force of the inner cuff 104 against the outer bladder 106. As such, the pressure sensor 602 measures the tracheal pressure, e.g. the pressure exerted by the cuff assembly 102 against the tracheal wall.

In an embodiment, the intercuff pressure sensor device 602 is electronically and communicatively attached to a lead 604 that extends from the pressure sensor 602 to a lead guide 606. The lead guide 606 protects the lead 604 and trachea. The intracuff pressure sensor device 602 communicates pressure measurements to a pressure regulation system over the lead 604. In another embodiment, the pressure sensor device 602 includes a wireless transmitter, such as an radio frequency identification (RFID) transmitter or Internet of Things (IoT) cellular type transmitter. The pressure sensor device 602 may then wirelessly transmit pressure measurements to the pressure regulation system using the wireless transmitter.

Additional pressure sensor devices may be positioned within the cuff assembly. For example, a pressure sensor device may be positioned in the inner cuff 104 to measure an intracuff pressure within the inner cuff 104. In addition, a pressure sensor device may be positioned within the outer bladder 106 to measure its pressure. Another pressure sensor device may be positioned on an outer surface of the bladder 106 to measure a tracheal pressure. Additional pressure sensor devices may be positioned within the endotracheal tube 102 or at the tip 224 of the endotracheal tube 102, to measure the pressure of the oxygenated air delivered to a patient.

Figure 7:
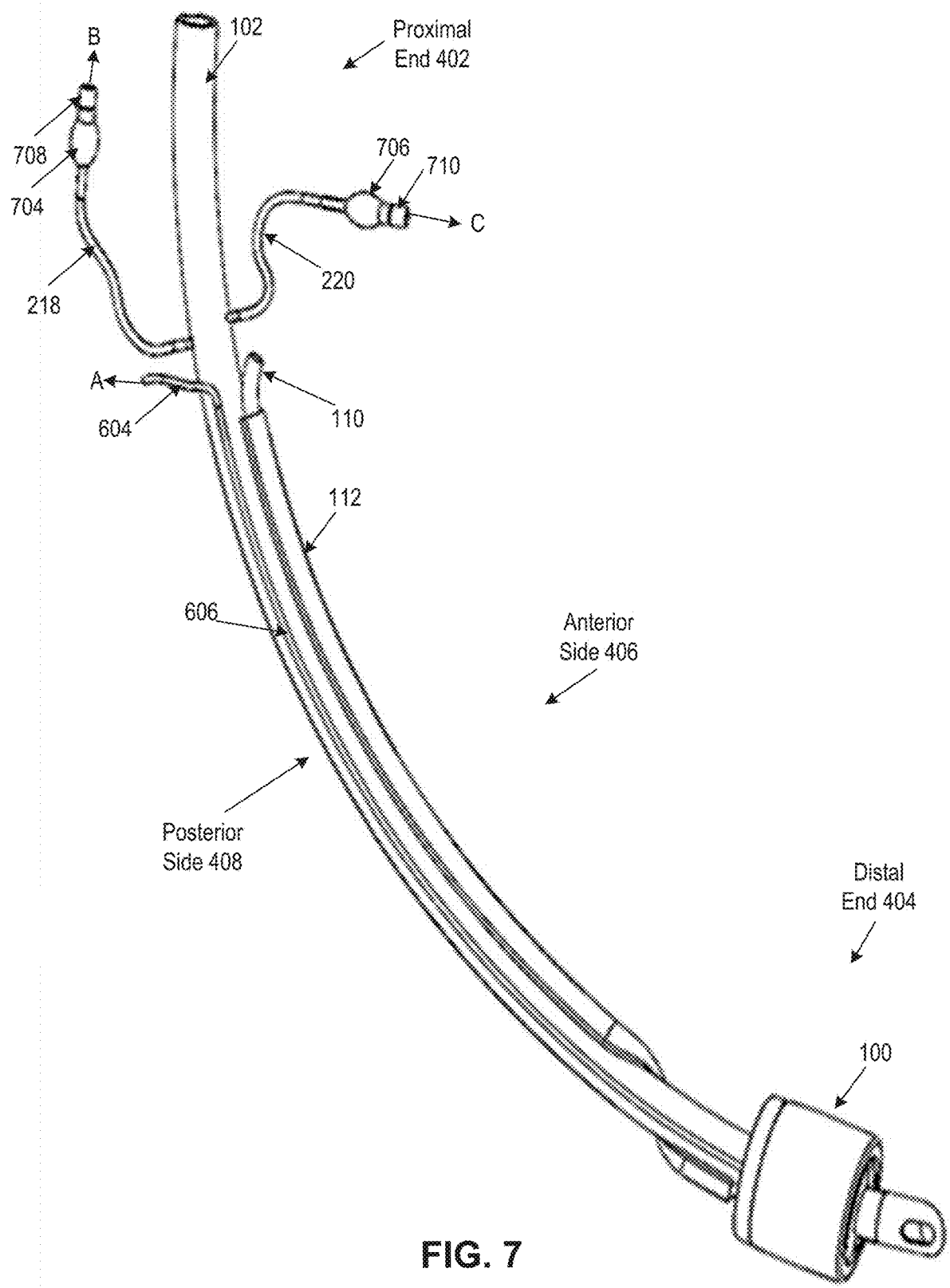
FIG. 7 illustrates an exemplary embodiment of the endotracheal tube with the cuff assembly.

FIG. 7 illustrates an exemplary embodiment of the endotracheal tube 102 with the cuff assembly 100. A lead guide 606 and the lead 604 therewithin extends from the cuff assembly 100 along an interior or exterior of the endotracheal tube 102 to a proximal end of the endotracheal tube 102. The lead 604 then connects to the pressure regulation system for communication of intercuff pressure measurements and/or power supply.

A first pilot balloon 704 is attached at a distal end of the first lumen 218, wherein the first lumen 218 fluidly couples to the outer bladder 106. The first pilot balloon 704 inflates along with the outer bladder 106 and may serve as an indication of the pressure in the outer bladder 106 and whether the outer bladder 106 is inflated.

Similarly, the second pilot balloon 706 is attached at an inferior end to the second lumen 220, wherein the second lumen 220 fluidly couples to the inner cuff. The second pilot balloon 706 inflates along with the inner cuff 104 and may serve as an indication of the pressure in the inner cuff 104 and whether the inner cuff 104 is inflated.

The proximal ends of both the first and second pilot balloons 704, 706 include first and second adapters 708, 710. The first and second adapters 708, 710 are coupled to air pumps in a pneumatic device, as described below.

Figure 8:
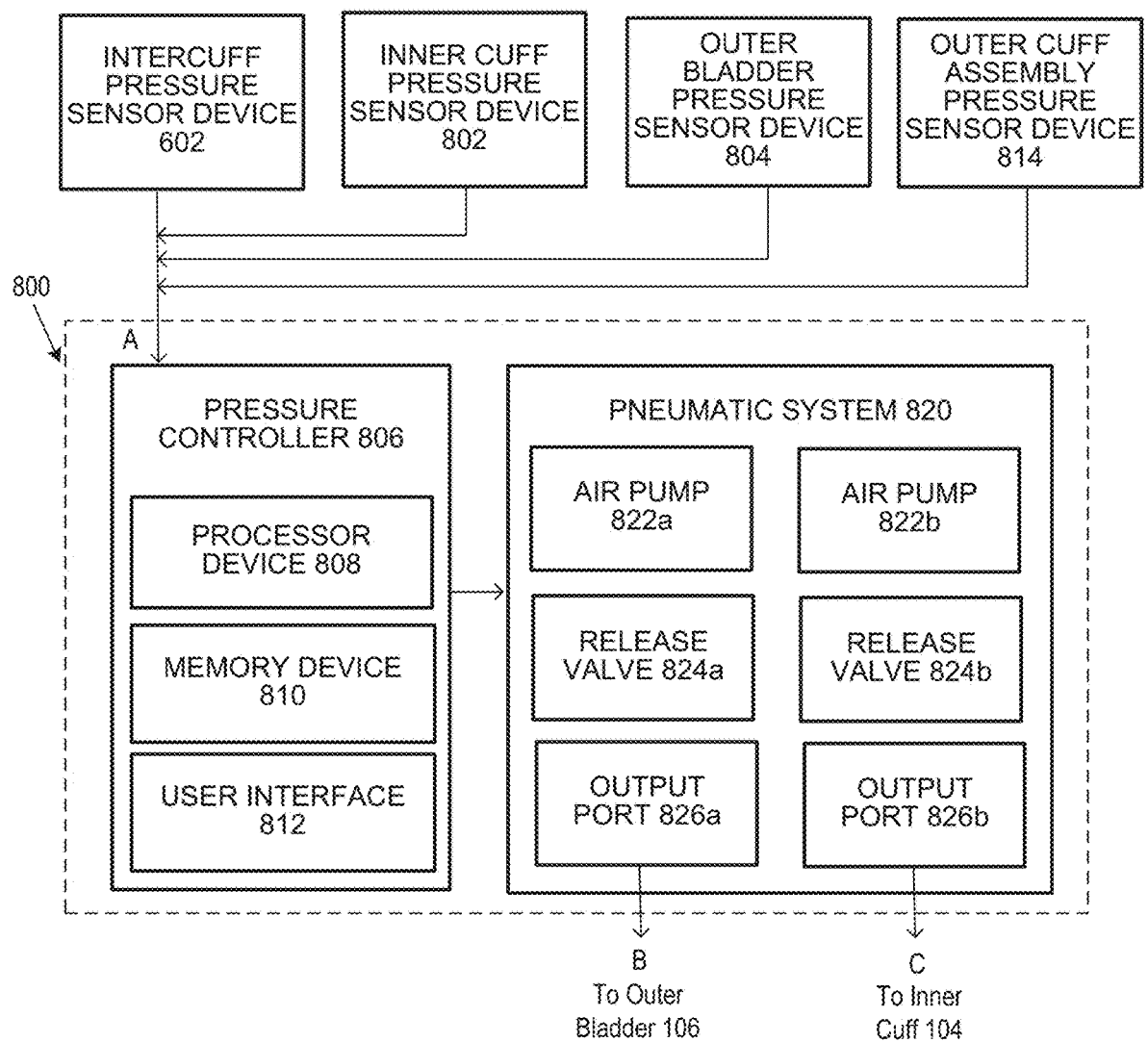
FIG. 8 illustrates a schematic block diagram of an exemplary embodiment of a pressure regulator and control system for the cuff assembly.

FIG. 8 illustrates a schematic block diagram of an exemplary embodiment of a pressure regulator and control system ("regulator system") 800 for the cuff assembly 100. The regulator system 800 fluidly communicates with and inflates and adjusts the pressure within the cuff assembly 100, e.g. when the endotracheal tube 102 is implanted into the patient's trachea. The pressure of the inner cuff 104 and the outer cuff bladder 106 of the cuff assembly 100 are monitored and controlled separately.

The regulator system 800 includes a pressure controller 806 and pneumatic system 820. The pressure controller 806 includes a processor device 808 and a memory device 810. The memory device 810 includes one or more non-transitory processor readable memories that store instructions which when executed by the processor device 808 or other components of the regulator system 800, causes the regulator system 800 to perform one or more functions described herein. The processor device 808 includes at least one processing circuit, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The memory device 810 includes a non-transitory memory device and may be an internal memory or an external memory, and may be a single memory device or a plurality of memory devices. The memory device 810 may be a read-only memory, random access memory, volatile memory, non-volatile memory, static memory, dynamic memory, flash memory, cache memory, and/or any non-transitory memory device that stores digital information.

The pressure controller 806 may be co-located with the pneumatic system 820 in a same physical device or located separately in a different device or encasement. The pressure controller 806 further includes a user interface 812. The user interface 812 generates user input and output (I/O) and includes one or more of a display, keyboard, touch screen, mouse, touchpad, gauge, switch, or other I/O device.

In use, a desired predetermined pressure setting is determined for the cuff assembly 100 by the pressure controller 806 in response to user input received by the user interface 812. Alternatively, a default pressure setting may be implemented, e.g. in absence of user input.

A different pressure setting may be set for the inner cuff 104 and the outer bladder 106. The pressure setting may be a predetermined pressure or a pressure range, e.g. typically within a plus or minus 2 cm H2O. For example, the pressure setting for the inner cuff may be a pressure (plus or minus 2 cm H2O) within the range of 10 cm H2O to 20 cm H2O. In contrast, the pressure setting for the outer inflating bladder may be a pressure (plus or minus 2 cm H2O) within the range of 50 cm H2O to 150 cm H2O. The inner cuff 104 thus operates in a pressure range that is less than the operational pressure range of the outer bladder 106. The pressure controller 806 further determines a frequency of measuring and adjusting the pressure of the cuff assembly 100, e.g. either through a user input or default setting.

The pneumatic system 820 includes a first pneumatic pathway for the outer bladder 106 that includes, e.g., a first air pump 822a and release valve 824a that fluidly couples with the outer bladder 106 through, e.g., output port 826a, adapter 708, pilot balloon 704 and lumen 218. The pneumatic system 820 further includes a different, second pneumatic pathway for the inner cuff 104 that includes a second air pump 822b and release valve 824b that fluidly couples with the inner cuff 104 through, e.g., output port 826b, adapter 710, pilot balloon 706 and lumen 220. Though two air pumps 822a, 822b are described herein, a single air pump may supply the pressurized air to the inner cuff 104 and the outer bladder 106, e.g. using a valve or switch between the two fluid pathways.

The pneumatic system 820 thus includes separate pneumatic pathways to fluidly increase or decrease the pressure in the air cuff 104 and the outer bladder 106 independently and separately. The pneumatic pathways may include separate air pumps 822a, 822b or a single air pump with a valve to switch between the pneumatic pathways for the outer bladder 106 and for the inner cuff 104.

In operation, the pressure controller 806 receives pressure measurements from one or more pressure sensor devices to regulate the pressure of the cuff assembly 100. For example, the intercuff pressure sensor device 602 is positioned between the inner cuff 104 and the outer bladder 106 and measures the radial force of the inner cuff 104 against the outer bladder 106. Another inner cuff pressure sensor device 802 may be positioned within the inner cuff 104 to measure intracuff pressure. An outer bladder pressure sensor device 804 may be positioned to measure the pressure within the outer bladder 106. A further outer cuff assembly pressure sensor device 814 may be positioned on an outer surface of the outer bladder 106 to further measure tracheal wall pressure. Additional pressure sensor devices may also be implemented. The pressure sensor devices generate and communicate pressure measurements to the pressure controller 806, e.g. either through a wired lead and/or a wireless transmitter.

The regulator system 800 includes a pressure feedback loop wherein the pressure controller 806 controls the pneumatic system 820 to adjust the pressures for both the inner cuff 104 and the outer bladder 106 responsive to the pressure measurements. The pressures of the inner cuff 104 and the outer bladder 106 are monitored and controlled separately. The pressure controller 806 signals the pneumatic system 820 to add or release air to the outer bladder 106 and/or the inner cuff 104. For example, to adjust the pressure in the outer bladder 106, the pressure controller 806 may signal the air pump 822a to add air to the outer bladder 106 or signal the release valve 824a to release air from the outer bladder 106. In another example, to adjust the pressure in the inner cuff, the pressure controller 806 may signal the air pump 822b to add air to the inner cuff 104 or signal the release valve 824b to release air from the inner cuff 104.

The regulator system 800 monitors the pressure measurements and adjusts the pressure, firstly of the outer bladder 106 and secondly of the inner cuff 104, automatically to achieve the predetermined pressure settings, e.g. preselected by an operator or by default. The pressure controller 806 may monitor and adjust the pressure of the cuff assembly 100 continuously or may monitor and adjust the pressures at predetermined intervals. The regulator system 800 may further include visible and/or audible alarms in the event of unsafe pressure measurements.

Figure 9:
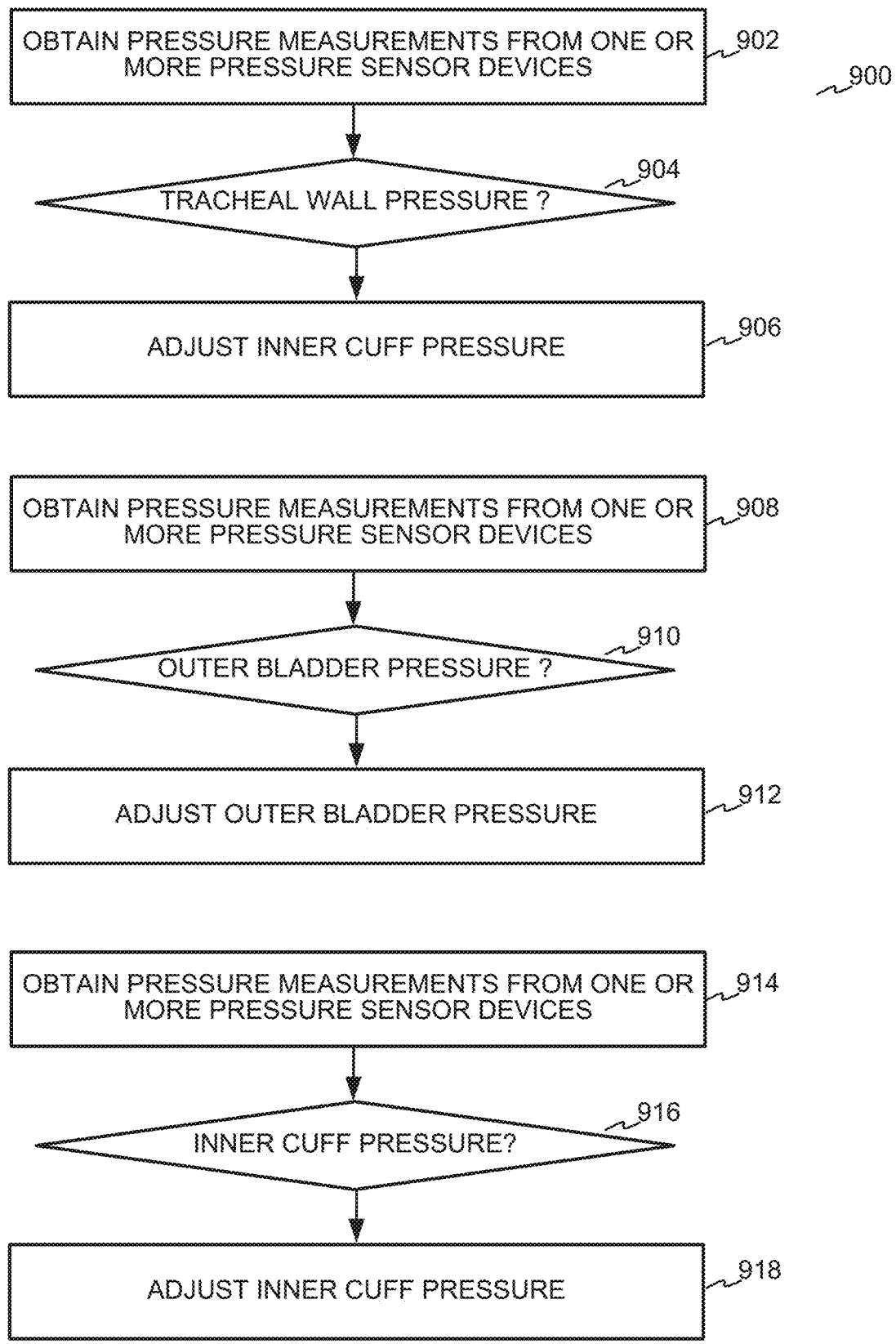
FIG. 9 illustrates a flow chart of an embodiment of one or more methods for monitoring and controlling the pressure of the cuff assembly.

FIG. 9 illustrates a flow chart of an embodiment of one or more methods 900 for monitoring and controlling the pressure of the cuff assembly 100, e.g. by the regulator system 800. At step 902, one or more pressure measurements relating to the tracheal wall pressure are obtained by the regulator system 800 from one or more pressure sensor devices. Using these pressure measurements, the regulator system 800 determines whether the tracheal pressure, e.g. the pressure exerted by the cuff assembly 100 on the tracheal wall, is within a predetermined pressure range at Step 904. The pressure measurements may be from the intercuff pressure sensor device 602 between the inner cuff 104 and the outer bladder 106 and/or from one or more pressure sensors 814 located on an outer surface of the outer bladder 106. When the tracheal pressure exceeds a predetermined pressure range, the system 800 decreases at least the pressure in the inner cuff 104 at Step 906. For example, the regulator system 800 may control the release valve 824b to release air from the inner cuff 104. Since the tracheal mucosal blood flow may be compromised at applied pressures above 30 cm H2O (22 mmHg), when the measured tracheal pressure exceeds 30 cm H2O (22 mmHg), then the regulator system 800 may decrease at least the pressure of the inner cuff 104.

When the tracheal pressure is less than a predetermined pressure range, the regulator system 800 increases at least the pressure in the inner cuff 104 at Step 906. For example, the regulator system 800 may control the air pump 822b to pump air into the inner cuff 104. In addition, the pressure of the outer bladder 106 may also be adjusted. These steps may be performed at preset intervals or continuously.

At step 908, one or more pressure measurements relating to the outer bladder pressure are obtained by the regulator system 800 from one or more pressure sensor devices. Using these pressure measurements, the regulator system 800 determines whether the pressure of the outer bladder 106 is within a predetermined pressure range at step 910. For example, the pressure measurements may be from an a pressure sensor device 804 located within the outer bladder 106 or at the pilot balloon 704 for the outer bladder 106. When the outer bladder pressure is less than or more than the predetermined pressure range, the regulator system 800 increases or decreases the pressure in the outer bladder 106 at Step 912. For example, the regulator system 800 may control the air pump 822a to pump air into the outer bladder 106 when its pressure is below the predetermined pressure range or control the release valve 824a to release air from the outer bladder 106 when its pressure is above the predetermined pressure range. The outer bladder 106 may have a predetermined pressure range of 50 cm H2O to 150 cm H2O.

At step 914, one or more pressure measurements relating to the inner cuff pressure are obtained by the regulator system 800 from one or more pressure sensor devices. Using these pressure measurements, the regulator system 800 determines whether the pressure of the inner cuff 104 is within a predetermined pressure range at step 916. For example, the pressure measurements may be from an a pressure sensor device 802 located within the inner cuff 104 or at the pilot balloon 706 for the inner cuff 104. When the inner cuff pressure is less than or more than the predetermined pressure range, the regulator system 800 may increases or decrease the pressure in the inner cuff 104 at Step 918. For example, the regulator system 800 may control the air pump 822b to pump air into the inner cuff 104 when its pressure is below the predetermined pressure range or control the release valve 824b to release air from the inner cuff 104 when its pressure is above the predetermined pressure range. The inner cuff is a low-pressure inflatable cuff and may have a predetermined pressure range of 10 cm H2O to 20 cm H2O.

The pressure of the inner cuff 104 and the outer cuff bladder 106 of the cuff assembly 100 are thus controlled separately using separate pneumatic pathways, e.g., separate air pumps 822 and/or release valves 824 and separate air lumens, 218, 220. The pressure of the more inelastic outer bladder 106 is maintained at a higher pressure than the pressure of the more elastic inner cuff. The pressure controller 802 may thus independently adjust a pressure of the inner cuff 104 or the outer bladder 106 to adjust the tracheal pressure.

An intracuff pressure sensor 602 between the inner cuff 104 and the outer bladder 106 provides a tracheal pressure measurement. The pressure controller 802 may independently adjust a pressure of the inner cuff 104 and/or the outer bladder 106 to adjust the tracheal pressure, e.g. when the tracheal pressure exceeds an unsafe threshold or falls below a threshold.

The cuff assembly 100 and the regulator system 800 thus help to reduce microaspiration and infection of the lungs by maintaining a good seal with the tracheal wall but without unduly harming the tracheal wall. The systems provide an improved airway seal and cause a minimal damage to the airway.

Embodiments of the Secretion Clearance System

A mechanically ventilated (MV) patient experiences a physiologically altered milieu: reduced ability to clear oral and nasal secretions, diminished tracheobronchial mucociliary clearance, increased accumulation of secretions in the lungs and bronchus, reduced cough reflex, and increased likelihood of gastric reflux. The combined effect of all these factors is to predispose the mechanically ventilated patient to ventilator-associated pneumonia (VAP), an infection of the lungs that develops in patients, typically after 48 hours of being on mechanical ventilation.

An accumulation of secretions above an endotracheal tube (ETT) cuff (including but not limited to the cuff assembly 100 described herein) in MV patients is a normal physiological phenomenon. The sources of secretions are oral cavity, sinuses, and stomach (the "orogastric secretions"). It is known that under normal conditions, the oral cavity and sinuses produce up to 3 liters per day of secretions. Again, that does not include gastric refluxate, which may be significant. While a healthy person is capable of eliminating and/or managing secretions, a ventilated patient cannot. Instead, in a ventilated patient, secretions in the trachea accumulate above the ETT cuff or leak past the ETT cuff and into the trachea and lungs.

The concern with accumulation of secretions above the ETT cuff is that secretions are loaded with microorganisms including bacteria and fungus. Since the secretions are heavily contaminated, they should be kept away from sterile organs of the human body. The lungs are one of those sterile organs. As such, it becomes imperative for the treating physician to prevent secretions from leaking into the patient's lungs.

The ETT cuff can be a powerful aspiration-deterrent mechanism. When inflated, the ETT cuff is supposed to contact the tracheal wall circumferentially resulting in a complete seal. The ETT cuff, unfortunately, is known to not provide an efficient seal principally due to the formation of wrinkles or folds from the over-sized cuff as discussed above.

One strategy to combat VAP is to enhance the occlusive functionality of ETT cuffs, e.g. improve the sealing capability of ETT cuffs, thereby reducing secretions leaking into the lungs as discussed herein with the cuff assembly 100. While this strategy is helpful, if secretions are allowed to accumulate above the ETT cuff, eventually the sheer pressure of the secretions will likely cause the secretions to leak into the lungs. In addition to an effective tracheal occlusion, therefore, an effective means to clear secretions is also needed.

Current systems to clear secretions include a suction tube proximate to a proximal end of the ETT cuff. However, the configuration of the suction tube opening is known to cause direct injury and suction trauma to the tracheal mucosa. Suction tube opening is configured to render it vulnerable to occlusion by the cuff wall. In addition, due to its small size, the suction tube easily occludes. A larger suction tube may increase bulkiness of the ETT, significant enough to make the intubation process more difficult. In addition, when the suction tube is integrated into the ETT, and the suction tube occludes, it is necessary to change out the entire ETT and ETT cuff. As such, there is a need for an improved secretion clearance system.

Figure 10A:
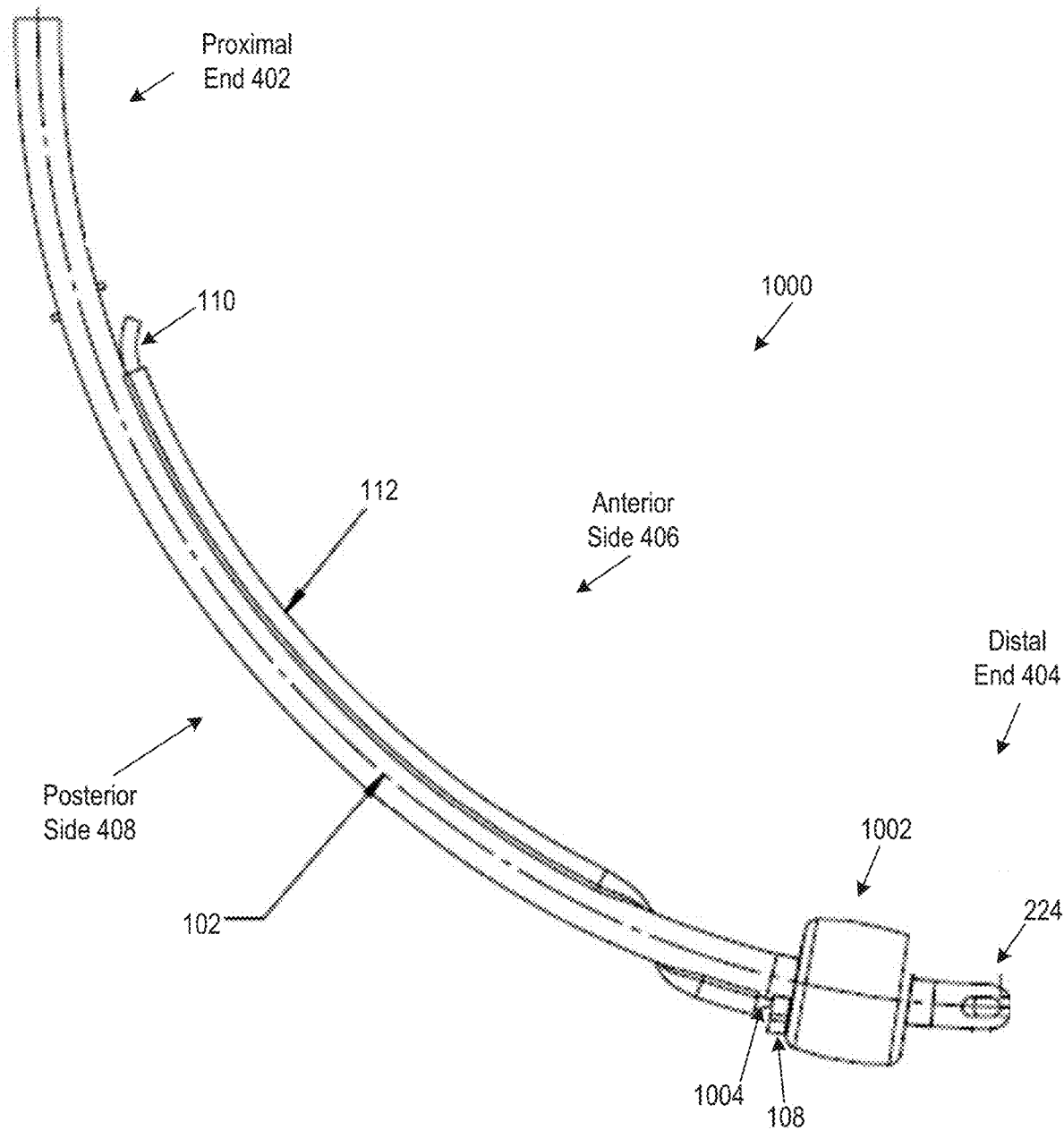
FIG. 10A illustrates an exemplary embodiment of a secretion clearance system.

FIG. 10A illustrates an embodiment of a secretion clearance system 1000 that provides an improved system and method to effectively clear secretions from an ETT cuff 1002. The secretion clearance system 1000 comprises the secretion collection receptacle 108, a suction catheter 110 and catheter guide 112. The secretion clearance system 1000 is shown implemented with a endotracheal tube 102 but may be implemented with other medical devices, such as other types of airway tubes or stents. The ETT cuff 1002 may include the cuff assembly 100 described herein, or may include other types of cuffs, such as an HVLP cuff or LVHP cuff.

The secretion collection receptacle 108 is positioned on a proximal or proximal end of the ETT cuff 1002 on a posterior side of the endotracheal tube 102. When a patient is in a prone position, such as typical with intubated patients, secretions will tend to accumulate on a posterior side of the trachea. Since the receptacle 108 is positioned on the posterior side of the ETT 102 and ETT cuff 1002, it will more likely collect the accumulated secretions. In other embodiments, the receptacle 108 may encircle the ETT 102. In other embodiments, the receptacle 108 encompasses only a portion of the circumference, such as 180 degrees of the circumference, on the posterior side 408 of the endotracheal tube (ETT) 102.

The catheter 110 is preferably a thin-walled, non-collapsible, and flexible hollow channel or tube. The catheter 110 is configured to evacuate the receptacle 108 and so at least a tip 1004 of the catheter 110 is positioned in or adjacent to the receptacle 108. The catheter tip 1004 is positioned on a posterior side of the endotracheal tube 102 and the ETT cuff 1002. The catheter tip 1004 is thus in a better position to suction and remove accumulated secretions in a prone, intubated patient that tend to accumulate on a posterior side of the trachea and receptacle 108.

A catheter guide 112 encloses the suction catheter 110 to provide protection to the catheter 110. The pre-formed channel of the catheter guide 112 is positioned externally on the outer surface of the ETT 102. At a proximal end 402 of the ETT 102, the catheter guide 112 extends along the anterior side 406 of the outer surface of the ETT 102. At the distal end 404 of the ETT 102, the catheter guide 112 extends around a half circumference of the ETT 102 to the posterior side 408 of the distal end 404 of the ETT 102.

A prone, intubated patient includes an opening on the anterior side of the trachea between the vocal cords. Since the catheter guide 112 is positioned anteriorly on the ETT 102 at the proximal end 402, the catheter guide 112 may rest within this opening for the vocal cords without applying undue pressure onto the trachea. Due to this positioning between the vocal cords, the catheter guide 112 and the suction catheter 110 may have an increased diameter. A larger diameter in the catheter 110 may help prevent occlusion. In one example, the catheter 110 may have an inner diameter of approximately 5 mm or an inner diameter in a range of 2 mm to 10 mm.

At the distal end 404 of the ETT 102, the catheter guide 112 and catheter 110 rotate a half circumference around the ETT 102 to a posterior side 408 of the ETT 102 for improved collection of secretions that tend to accumulate on the posterior side of the trachea and ETT cuff 1002. The catheter guide 112 may extend into the collection receptacle 108 or in proximity to the collection receptacle 108. The catheter tip 1004 extends into the collection receptacle 108 or in proximity to the collection receptacle 108. In one example, the catheter 110 and tip 1004 comprise a semirigid material, such as one or more of: polyvinyl chloride (PVC), silicone, neoprene, polyisoprene, or polyurethane (PU). The size of the catheter 110 may be between 7 and 12 French, e.g. a circumference of 7.33 mm to 12.57 mm. The tip 1004 of the catheter in an embodiment includes at least two openings, e.g. one on each of opposing sides of the tip 1004, to lessen the possibility of catheter occlusion.

Figure 10B:
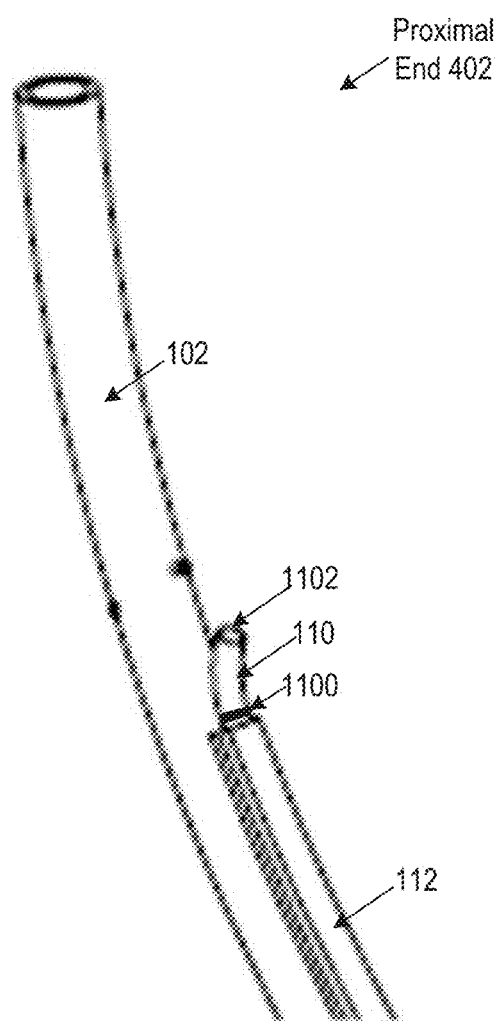
FIG. 10B illustrates an exemplary embodiment of a proximal end of the catheter and catheter guide in more detail.

FIG. 10B illustrates an embodiment of a proximal end of the suction catheter 110 and catheter guide 112 in more detail. In an embodiment, the catheter 110 includes a depth indicator 1100 that provides an indication of proper positioning of the catheter 110 in the catheter guide 1102. The depth indicator 1100 may include markings as a guide. In another embodiment, the depth indicator 1100 is a raised ridge that prevents further insertion of the catheter 110 into the catheter guide 112.

A proximal catheter end 1102 is configured to connect to a vacuum source using suction tubing. The catheter 110 may be connected to the vacuum source intermittently or continuously. When connected, the vacuum source may operate continuously or intermittently to clear the secretions in the receptacle 108. The superior catheter end 1102 is further adaptable to a syringe or other means for irrigation. An alarm may be triggered when the catheter becomes occluded.

Figure 11A:
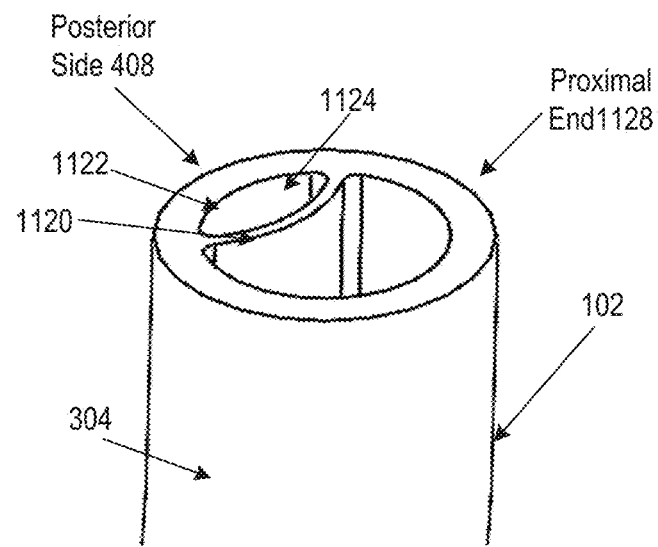
FIG. 11A illustrates another exemplary embodiment of a proximal end of an internal catheter guide.
Figure 11B:
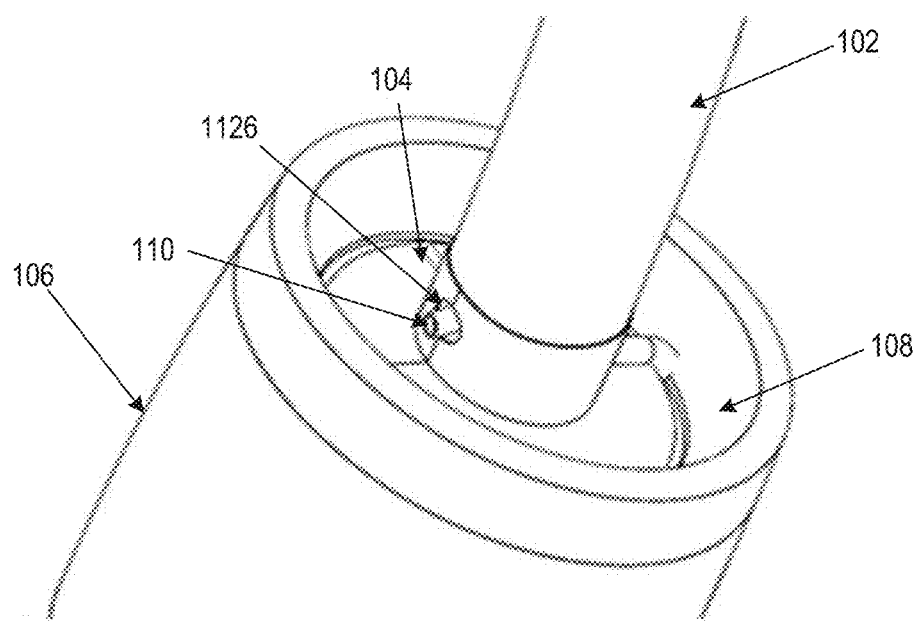
FIG. 11B illustrates another exemplary embodiment of a secretion clearance receptacle and suction catheter with an internal catheter guide.

FIGS. 11A and 11B illustrate exemplary embodiments of a hollow, suction channel 1122 formed within the endotracheal tube 102. In this embodiment, an interior suction channel 1122 is positioned internally within the endotracheal tube 102. For example, the suction channel 1122 may be formed by a portion of an interior wall 1124 of the endotracheal tube 102 and a longitudinal partition 1120 that extends across the portion of the interior wall 1124. The section of the interior wall 1124 and the longitudinal partition 1120 are positioned on a posterior side 408 of the endotracheal tube 102 to form a hollow tube or lumen. The suction channel 1122 extends from the proximal end of the endotracheal tube 102 to a position in the endotracheal tube 102 alongside or in proximity to the secretion receptacle 108.

In one embodiment, the suction channel 1122 is in fluid communication with the secretion receptacle 108 through an opening 1126 formed through a wall of the endotracheal tube 102. The opening 1126 is positioned on a posterior side of the endotracheal tube 102 within or in proximity to the receptable 108. The secretions are then evacuated from the secretion receptacle 108, through the opening 1126, through the suction channel 1122 to a proximal end 1128 of the endotracheal tube 102. A suction catheter (not shown) may be fluidly coupled to the proximal end 1128 of the suction channel 1122 and to a vacuum, without the catheter continuing through the lumen of the suction channel 1122.

In another embodiment, e.g. shown in FIG. 11B, a catheter 110 may be inserted into the suction channel 1122. In this embodiment, the suction channel 1122 is configured to fit a suction catheter 110. For example, a suction catheter 110 may have an outer diameter of 4 mm. The suction channel 1122 may then have an opening greater the 4 mm, such as 4.1-4.5 mm, such that the suction catheter 110 is able to slide through the catheter guide in case of removal and/or insertion of a new suction catheter 110. The opening 1126 has a diameter or size configured to accommodate a distal end of a suction catheter 110. The distal end of the suction catheter 110 extends outward from the opening 1126 into the receptacle 108. The suction catheter 110 fluidly communicates with the receptacle 108 to remove accumulated secretions. The catheter guide 1122 may include a slanted surface or bottom across the diameter of the catheter guide at the opening 1126 to guide and position the distal end of the catheter 110 through the opening 1126.

Figure 12A:
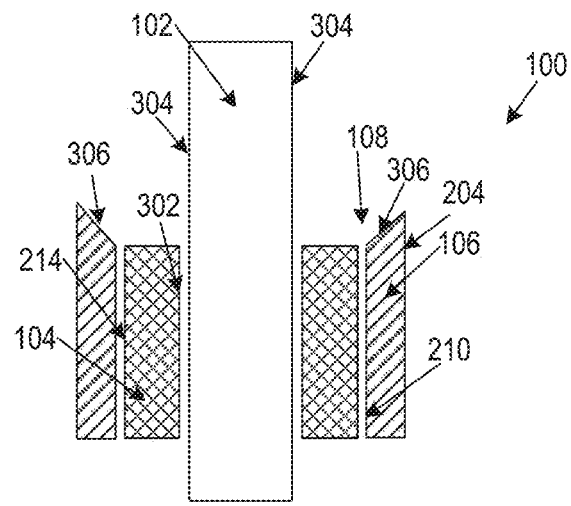
FIGS. 12A-C illustrate schematic block diagrams of various exemplary embodiments of the secretion collection receptacle implemented with the cuff assembly.
Figure 12B:
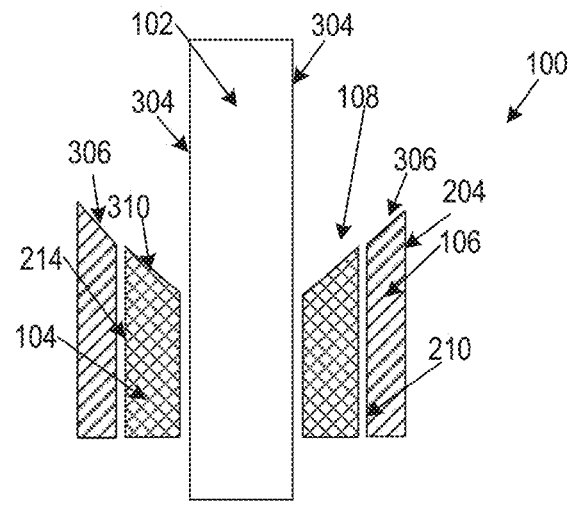
Figure 12C:
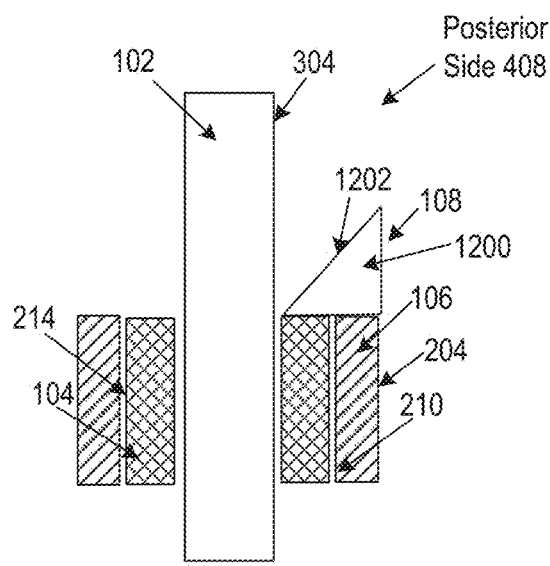

FIGS. 12A-C illustrate schematic block diagrams of various embodiments of the secretion collection receptacle 108 implemented with the cuff assembly 100, e.g. including the inner cuff 104 and the outer bladder 106. In FIG. 12A, the secretion collection receptacle 108 is formed using an outer surface 204 of the outer bladder 106. For example, a portion of the outer surface 204 of the outer bladder 106, e.g. on a proximal surface 306 of the outer bladder 106, extends beyond the outer surface 214 of the inner cuff 104 to form an outer wall. The proximal end 306 of the outer bladder 106 may slant inwardly towards the outer surface 214 of the inner cuff 104 to form a valley or trough around the endotracheal tube 102. The valley or trough forms the secretion collection receptacle 108. The floor of the collection receptacle 108 is defined by the proximal surface of the inner cuff 104, whose surface may or may not be reinforced with a stiffer, less elastic material than other portions of the inner cuff 104.

The length of the outer wall 204 of the receptacle 108 may range between 2 mm to 15 mm. The receptacle 108 may span 180 degrees on the posterior side of the cuff assembly 100. The receptacle 108 helps to protect the tracheal wall from suction trauma or direct injury from the suction catheter 110. The outer wall 204 forming the receptacle 108 may include a PVC sheet to oppose and seal the tracheal wall and allow the secretion to flow into the well. The rigid PVC sheet helps to prevent leakage of the secretion. The floor of the receptacle 108 may include a thin plastic sheet extending from the junction between the outer surface of the inner cuff and the inner surface of the outer bladder.

FIG. 12B illustrates an embodiment in which the proximal surfaces 306, 310 of both the outer bladder 106 and the inner cuff 104 slant inwardly towards the outer surface 304 of the endotracheal tube 102 to form a valley or trough around at least a portion of the endotracheal tube 102. The valley or trough forms the secretion collection receptacle 108.

In FIG. 12C, a separate structure 1200 attached to a proximal end of the cuff assembly, on a posterior side 408 of the ETT 102, forms the secretion collection receptacle 108. The separate structure 1200 may be attached to one or both of the inner cuff 104 and outer bladder 106. The separate structure 1200 may include a slanted top surface 1202 that slants inwardly towards the outer surface 304 of the ETT 102 to form a valley or trough.

Figure 13A:
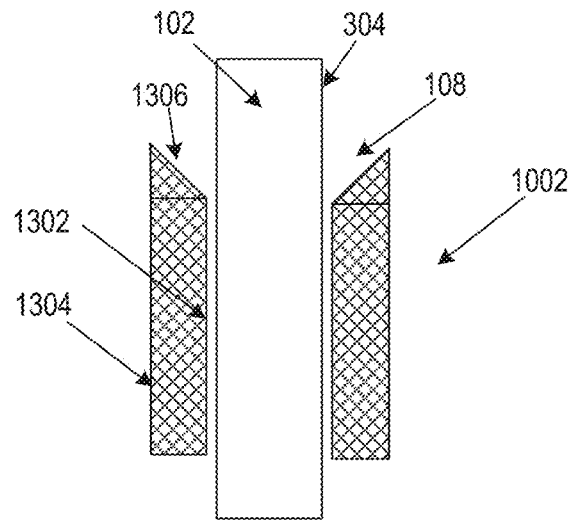
FIGS. 13A-B illustrate schematic block diagrams of various exemplary embodiments of the secretion collection receptacle implemented with other types of endotracheal cuffs.
Figure 13B:
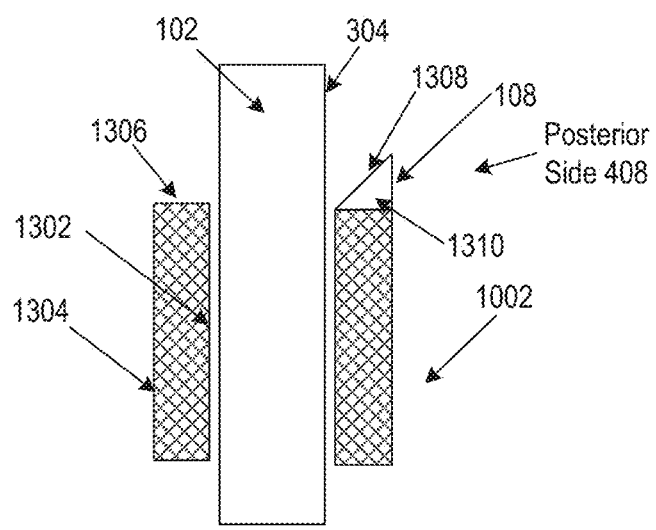

FIGS. 13A-B illustrate schematic block diagrams of various embodiments of the secretion collection receptacle 108 implemented with other types of ETT cuffs 1002. The other types of ETT cuffs 1002 may include, e.g., an HVLP or LVHP cuff with a single balloon or may include other types of medical cuffs, such as use with stents or other medical devices.

In FIG. 13A, the receptacle 108 is formed by at least a portion of an outer wall 1304 of the ETT cuff 1002, e.g. on a proximal end 1306 of the ETT cuff 1002. The outer wall 1304 extends beyond the inner wall 1302 and may slant towards the outer surface 304 of the ETT 102 to form a valley or trough around the ETT 102. The valley or trough forms the secretion collection receptacle 108.

In FIG. 13B, a separate structure 1310 attached to a proximal end 1306 of the ETT cuff 1002, e.g. on a posterior side 408 of the ETT 102, forms the secretion collection receptacle 108. The separate structure 1310 may include a slanted top surface 1308 that slants inwardly towards the outer surface 304 of the ETT 102 to form a valley or trough.

In these embodiments in FIGS. 12A-D and 13A-B, the secretion collection receptacle 108 may encircle the ETT 102 fully or only partially. The tip of the suction catheter 110 lies within the trough of the secretion collection receptacle 108 or in close proximity thereto. The collection receptacle 108 helps to protect the tracheal wall from suction trauma or direct injury from the suction catheter 110. In addition, the catheter guide 112 holds the tip of the suction catheter 110 in position near the outer surface 304 of the ETT 102 and inside or in proximity to the collection receptacle 108. This positioning of the tip of the catheter 110 also helps to protect the tracheal wall.

The secretion clearance system 1000 thus helps to reduce the possibility of injuring the tracheal mucosa. It also helps to reduce blocking of the openings in the tip 1004 of the catheter 110 by the cuff wall, e.g. helps to prevent the cuff being sucked into the catheter 110. The retractable catheter 110 in the catheter guide 112 makes it no more cumbersome to intubate the ETT 102. Moreover, due to the placement of the catheter guide, a larger diameter catheter 110 may be employed which reduces the chance of occlusion.

The cuff assembly 100, regulator system 800, and the secretion evacuation system 1000 improve the protection and safety of intubated patients. The cuff system 100 and the regulator system 800 maintain an improved seal with the tracheal wall that reduces leakage of secretions and infection of the lungs without unduly harming the tracheal wall. The secretion clearance system 1000 also helps to reduce the possibility of injuring the tracheal mucosa by using a secretion receptacle 108 and catheter guide 112. It also helps to reduce blocking of the openings in the tip 1004 of the catheter 110 by the secretions or the material of the cuff. Additional or alternative advantages and improvements are possible in one or more of the embodiments described in the specification and/or the claims.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled," "coupled to," "connected to" and/or "connecting" or "interconnecting" includes direct connection or link between nodes/devices and/or indirect connection between nodes/devices via an intervening item. As may further be used herein, inferred connections (i.e., where one element is connected to another element by inference) includes direct and indirect connection between two items in the same manner as "connected to." As may be used herein, the terms "substantially" and "approximately" provides an industry-accepted tolerance for its corresponding term and/or relativity between items.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A medical device, comprising:
an endotracheal tube configured to fit within a trachea; and
a cuff assembly implemented at an inferior end of the endotracheal tube, including:
an inflatable inner cuff with an inner surface and an outer surface, wherein the inner surface is positioned adjacent to the endotracheal tube and wherein the inner cuff has a first elasticity; and
an inflatable outer bladder positioned adjacent to the outer surface of the inner cuff, wherein the outer bladder has a second elasticity that is less than the first elasticity of the inner cuff, wherein the inner cuff is configured to be inflated within a first pressure range and wherein the outer bladder is configured to be inflated within a second pressure range, wherein the first pressure range is less than the second pressure range.

2. The medical device of claim 1, wherein the inner cuff is configured to be inflated to a first pressure within the first pressure range of 10 cm $H_2O$ to 20 cm $H_2O$ and the outer bladder is configured to be inflated to a second pressure within the second pressure range of 50 cm $H_2O$ to 150 cm $H_2O$.

3. The medical device of claim 1, wherein an outer surface of the outer bladder is configured to have a relatively smooth surface during inflation.

4. The medical device of claim 1, further comprising:
a first inflation lumen coupled to an interior of the inner cuff; and
a second inflation lumen coupled to an interior of the outer bladder.

5. The medical device of claim 1, wherein the inner cuff comprises a relatively elastic material, wherein the relatively elastic material includes one or more of: silicone, latex, polyvinyl chloride (PVC), neoprene, polyisoprene, or polyurethane (PU).

6. The medical device of claim 1, wherein the outer bladder comprises a relatively inelastic material, wherein the relatively inelastic material includes one or more of: polyethylene teraphthalate (PETP), low-density polyethylene (LDPE), polyvinyl chloride (PVC), silicone, neoprene, polyisoprene, or polyurethane (PU).

7. The medical device of claim 1, further comprising:
a secretion collection receptacle positioned at a proximal end of the cuff assembly; and
a suction channel including a distal end in proximity to the secretion collection receptacle and a proximal end of the suction channel at a proximal end of the endotracheal tube, wherein the proximal end of the suction channel is in fluid communication with a vacuum.

8. The medical device of claim 7, wherein the secretion collection receptacle comprises:
an outer wall of the cuff assembly that extends proximally from a proximal surface of the cuff assembly forming a trough for collection of secretions, wherein the trough is positioned at least on a posterior side of the endotracheal tube; and
a proximal slanted surface that slants inwardly from the outer wall towards the top surface of the cuff assembly forming the trough for collection of secretions.

9. The medical device of claim 7,
wherein the secretion collection receptacle includes an outer wall extending from a proximal end of the outer bladder to form a trough with a proximal surface of the inner cuff and/or a proximal surface of the outer bladder.

10. The medical device of claim 7, wherein the suction channel includes a catheter, and further comprising:
a catheter guide configured for holding the catheter, wherein the catheter guide is positioned on an anterior side of an outer surface at a proximal end of the endotracheal tube; and
wherein the catheter guide rotates circumferentially to a position on a posterior side of the outer surface at a distal end of the endotracheal tube.

11. The medical device of claim 7, wherein the suction channel is positioned internally to the endotracheal tube and extends on a posterior portion of an interior wall of the endotracheal tube; and
wherein the endotracheal tube forms an opening in proximity to the secretion collection receptacle, wherein the hollow channel is in fluid communication with the secretion collection receptacle through the opening for evacuation of secretions.

12. A medical device, comprising:
an endotracheal tube configured to fit within a trachea;
a cuff assembly implemented at an inferior end of the endotracheal tube, including:
an inflatable inner cuff with an inner surface and an outer surface, wherein the inner surface is positioned adjacent to the endotracheal tube and wherein the inner cuff has a first elasticity;
an inflatable outer bladder positioned adjacent to the outer surface of the inner cuff, wherein the outer bladder has a second elasticity that is less than the first elasticity of the inner cuff; and
a pressure regulator configured to:
adjust a first pressure in the inner cuff using a first pneumatic pathway; and
adjust a second pressure in the outer bladder using a different, second pneumatic pathway, wherein the first pressure in the inner cuff is less than the second pressure in the outer bladder.

13. The medical device of claim 12, further comprising:
a pressure sensor device positioned between the inner cuff and the outer bladder, wherein the pressure sensor device measures an intercuff pressure.

14. The medical device of claim 13, wherein the pressure regulator is configured to at least adjust the first pressure in the inner cuff and the second pressure in the outer bladder in response to the intercuff pressure.

15. An endotracheal tube with a cuff assembly, comprising:
an inflatable inner cuff with an inner surface and an outer surface, wherein the inner surface is positioned adjacent to the endotracheal tube and wherein the inner cuff has a first elasticity;
a first lumen extending from the endotracheal tube to the inner cuff, wherein the first lumen is fluidly coupled to the inner cuff;
an inflatable outer bladder positioned adjacent to the outer surface of the inner cuff, wherein the outer bladder has a second elasticity that is less than the first elasticity of the inner cuff; and
a second lumen extending from the endotracheal tube to the outer bladder, wherein the second lumen is fluidly coupled to the outer bladder.

16. The endotracheal tube with the cuff assembly of claim 15, further comprising:
  a pressure regulator system configured to maintain a first pressure within the inner cuff using the first lumen to add or remove air from the inner cuff and to maintain a second pressure within the outer bladder using the second lumen to add or remove air from the outer bladder, wherein the first pressure is less than the second pressure.

17. The endotracheal tube with the cuff assembly of claim 16, wherein the pressure regulator system comprises:
  a first air pump and a first release valve fluidly coupled to the first lumen and configured to add or remove the air from the inner cuff; and
  a second air pump and a second release valve fluidly coupled to the second lumen and configured to add or remove the air from the outer bladder.

18. The endotracheal tube with the cuff assembly of claim 16, further comprising:
  a pressure sensor device positioned between the inner cuff and the outer bladder, wherein the pressure sensor device measures an intercuff pressure; and
  wherein the pressure regulator system is configured to adjust the first pressure in the inner cuff and the second pressure in the outer bladder in response to the intercuff pressure.

19. A medical device, comprising:
an endotracheal tube configured to fit within a trachea;
a cuff assembly implemented at an inferior end of the endotracheal tube, including:
  an inflatable inner cuff with an inner surface and an outer surface, wherein the inner surface is positioned adjacent to the endotracheal tube and wherein the inner cuff has a first elasticity;
  a first inflation lumen coupled to an interior of the inner cuff;
  an inflatable outer bladder positioned adjacent to the outer surface of the inner cuff, wherein the outer bladder has a second elasticity that is less than the first elasticity of the inner cuff; and
  a second inflation lumen coupled to an interior of the outer bladder.

\* \* \* \* \*